United States Patent [19]
Tam et al.

[11] Patent Number: 5,965,707
[45] Date of Patent: Oct. 12, 1999

[54] RIN2, A NOVEL INHIBITOR OF RAS-MEDIATED SIGNALING

[75] Inventors: See-Ying Tam; Mindy Tsai, both of Wellesley; Stephen J. Galli, Winchester, all of Mass.

[73] Assignee: Beth Israel Deaconess Medical Center, Boston, Mass.

[21] Appl. No.: 08/942,819

[22] Filed: Oct. 2, 1997

Related U.S. Application Data

[60] Provisional application No. 60/058,520, Sep. 11, 1997.
[51] Int. Cl.$^6$ .............................. A61K 38/16; C07K 1/00
[52] U.S. Cl. ............................................ 530/352; 530/350
[58] Field of Search ...................................... 530/350, 352

[56] References Cited

FOREIGN PATENT DOCUMENTS 0 666 314 A1   8/1995   European Pat. Off. .

OTHER PUBLICATIONS

Han, L., et al., "Protein Binding and Signaling Properties of RIN1 Suggest a Unique Effector Function", *Proc. Natl. Acad. Sci., U.S.A.*, 94:4954–4959 (1997).
Stenmark, H., et al., "Rabaptin–5 Is a Direct Effector of the Small GTPase Rab5 in Endocytic Membrane Fusion", *Cell*, 83:423–432 (1995).
Horiuchi, Hisanori et al., "A Novel Rab5 GDP/GTP Exchange Factor Complexed to Rabaptin–5 Links Nucleotide Exchange to Effector Recruitment and Function", *Cell*, 90:1149–1159 (1997).
Marshall, "Ras target proteins in eukaryotic cells", *FASEB J.* 9:1311–1318 (1995).
Boguski and McCormick, "Proteins regulating Ras and its relatives", *Nature* 366:643–654 (1993).
Marshall, "Ras effectors", *Curr. Opin. Cell Biol* 8:197–204 (1996).
Han and Colicelli, "A Human Protein Selected for Interference with Ras Function Interacts Directly with Ras and Competes with Raf1", *Mol. Cell. Biol.* 15(3):1318–1323 (1995).
Galli, "New Concepts About The Mast Cell", *New Engl. J. Med.* 328 (4) :257–265 (1993).
Ravtch and Kinet, "Fc Receptors", *Ann. Rev. Immunol.* 9:457–492 (1991).
Beaven and Metzger, "Signal transduction by Fc receptors: the FcεRI case", *Immun. Today* 14(5):222–226 (1993).
Gordon et al., "Mast cells as a source of multifunctional cytokines", *Immunol. Today* 11(12) :458–464 (1990).
Paul et al., "Lymphokine and Cytokine Production by FcεRI$^+$ Cells",*Adv. Immunol.* 53:1–29 (1993).
Jabril–Cuenod et al., "Syk–dependent Phosphorylation of Shc", *J. Biol. Chem.* 271(27):16268–16272 (1996).
Treisman, "Regulation of transcription by MAP kinase cascades", *Curr. Opin. Cell Biol.* 8:205–215 (1996).
Colicelli et al., "Expression of three mammalian cDNAs that interface with RAS function in *Saccharomyces cerevisiae*", *Proc. Natl. Acad. Sci. USA* 88:2913–2917 (1991).
Burd et al., "A Yeast Protein Related to a Mammalian Ras–Binding Protein, Vps9p, Is Required for Localization of Vacuolar Proteins", *Mol. Cell. Biol.* 16(5):2369–2377 (1996).
Levitzki, "Targeting Signal Transduction for Disease Therapy", *Current Opinion in Cell Biology*, 8:239–244 (1996).
Henkemeyer et al., "Vascular System Defects and Neuronal Apoptosis in Mice Lacking Ras GTPase–Activating Protein", *Nature* 377:695–701 (1995).
Bollag et al., "Loss of NF1 Results in Activation of the Ras Signaling Pathway and Leads to Aberrant Growth in Haematopoietic Cells", *Nature Genetics* 12:144–148 (1996).
Tam et al., "Use of mRNA Differential Display to Identify Novel Genes Up–Regulated in Mast Cells Stimulated with IgE and Antigen", *FASEB J.* (Abstract 1253) 10:A1216 (1996).
Tam and Galli, "Up–Regulation of a Novel Gene Transcript in PC12 Cells Stimulated with Nerve Growth Factor and Mast Cells Stimulated with Stem Cell Factor", *Soc. Neurosci. Abstr.* (Abstract 225.3) 22(1):555 (1996).

*Primary Examiner*—Paula K. Hutzell
*Assistant Examiner*—Lin Sun-Hoffman
*Attorney, Agent, or Firm*—Hamilton, Brook, Smith & Reynolds, P.C.

[57] ABSTRACT

Novel gene, rin2, and encoded protein are disclosed which can inhibit the functional response induced by Ras-dependent signaling pathways are disclosed. Methods of inhibiting or enhancing Ras-dependent signaling and methods of treatment utilizing Rin2 are also disclosed.

8 Claims, 8 Drawing Sheets

FIG. 3A

```
                                                                GCACGAGGGGCGCTGGGAGCGGCGGTCGGACGCCGCGGAGCCGCGGAGCAGGAAGAAG ATG      62
                                                                                                                                   Met        1
  1 AGC CTG AAG TCC GAA CGC AGG GGA ATT CAT GTG GAT CAA TCT GAG CTC TGC AAG AAG       122
 63 Ser Leu Lys Ser Glu Arg Arg Gly Ile His Val Asp Gln Ser Glu Leu Cys Lys Lys        21
  2 CTG TAC GGT TAC GGC AAC CCT GCC TGG CAG GGT TTC TGC TCC AAG TGC TGG AGG GAG       182
123 Leu Tyr Gly Tyr Gly Asn Pro Ala Trp Gln Gly Phe Cys Ser Lys Cys Trp Arg Glu        41
 22 TGC CAC AAG CGG CAG ATC CAA GAG GAC TGG GAA CTG GCA GAA CGA CTT                   242
183 Cys His Lys Arg Gln Ile Gln Glu Asp Trp Glu Leu Ala Glu Arg Leu                    61
 42 TAC CAC AAG CGG CAG ATC CAA GAG GAC TGG GAA CTG GCA GAA CGA CTT                   242
 42 TAT CAC AAG GCC CGG CAG ATC CAA GAG GAC TGG GAA CTG GCA GAA CGA CTT
 42 TAC CAC AAG GCC CAG ATC CAA GAG GAC TGG GAA CTG GCA GAA CGA CTT
 42 Tyr His Lys Ala Arg Gln Ile Gln Glu Asp Trp Glu Leu Ala Glu Arg Leu                61
243 CAG CGG GAG GAG GAA TTC GCC CAG AGC AGC CAG GCC CAG TCC CTC                       302
 62 Gln Arg Glu Glu Glu Phe Ala Gln Ser Ser Gln Ala Gln Ser Leu                        81
303 CAG CGG GAG GAG GAA TTC GCC CAG AGC AGC CAG GCC CAG TCC CTC                       362
 62 Gln Arg Glu Glu Glu Phe Ala Gln Ser Ser Gln Ala Gln Ser Leu                       101
303 ACC TTC TCC AAG TTC GAG GAG AAG AAC CGA GTC ACC ACA GTG                           362
 82 Thr Phe Ser Lys Phe Glu Glu Lys Asn Arg Val Thr Thr Val                           101
363 AAG AAG TTC TTC AGC GCC TCT AGA GCT GGA TCC GAA ATT CAG GCC AAA                   422
102 Lys Lys Phe Phe Ser Ala Ser Arg Ala Gly Ser Glu Ile Gln Ala Lys                   121
423 CTC CCC AGT CCC ATA AAC CGG CAA ACC AGC ATT GAG GAC GTG ACT AAG GAG               482
122 Leu Pro Ser Pro Ile Asn Arg Gln Thr Ser Ile Glu Asp Val Thr Lys Glu               141
483 GCT CCA TTT CTC AAG ACC TTC TCA CAA GAA GTC TAT AAA CAG ACG AAG                   542
142 Ala Pro Phe Leu Lys Thr Phe Ser Gln Glu Val Tyr Lys Gln Thr Lys                   161
543 TTC ATA GAC TTT TTG GAA GCA ATG CCT TAT AAA AGG GAT TTA AGC CAG TCA GAA TGT       602
162 Phe Ile Asp Phe Leu Glu Ala Met Pro Tyr Lys Arg Asp Leu Ser Gln Ser Glu Cys       181
603 ATG TTT GAA GCA ATG CCT TAT AAA AGG GAT TTA AGC CAG TCA GAA TGT
603 ATG TTC CTG GCA GAT TTC CAA AAT GTG GAT GAT CAG AGA GAA CAC CGT GGG AAA GTG CCT CCA       662
182 Met Phe Leu Ala Asp Phe Gln Asn Val Ala Asp Arg Glu His Arg Gly Lys Val Pro Pro    201
663 TAC AAG AAG GAG ATA ATG CAG ATC GAA CAG CAC ATC ATG GAT CGT CTC TAT AAA           722
202 Tyr Lys Lys Glu Ile Met Gln Ile Glu Gln His Ile Met Asp Arg Leu Tyr Lys           221
663 GAG AAA GTG GAG GAG ATA ATG CAG ATC GAA CAG CAC ATC ATG GAT CGT CTC TAT AAA
663 Glu Lys Val Glu Glu Ile Met Thr Arg Ala Ile Leu Tyr Lys
723 CCA GAG ACT GAT ACT GAT GAG CTG GAT CTC GCC ATT CAA AAA AGA                       782
222 Pro Glu Thr Asp Thr Asp Glu Leu Ala Ile Gln Lys Arg                                241
723 TTT GTG TTC TGC CCA GAG ACT GAT GAG CTG GAT CTC GCC ATT CAA AAA AGA
723 Phe Val Phe Cys Pro Glu Thr Asp Glu Leu Ala Ile Gln Lys Arg
783 TTC GCC CTG ACG TGG GTA CAC GAG CCT ATG CAG ATG GAG CTC ATG GAA GAA ATC            842
242 Phe Ala Leu Thr Trp Val His Glu Pro Met Gln Met Glu Leu Met Glu Glu Ile           261
843 ATC AGG GCC CTG CTG GAA CAC ATG CCT CAG ATG AAT GAG GAG TCA CAA AAG               902
262 Ile Arg Ala Leu Leu Glu His Met Pro Gln Met Asn Glu Glu Ser Gln Lys
843 CCT GAA GTG TCC GAC ATG GTG TGG ACG ATC ACA ATT GAG ATG GAC TCA AAG
843 Pro Glu Val Ser Asp Met Val Trp Thr Ile Thr Ile Glu Met Asp Ser Lys
843 Pro Glu Val Ser Asp Met Val Trp Thr Ile Thr Ile Glu Met Asp Ser Lys               281
903 CGT GTG CCT CGG GAC AAG CGG CTG GCC ATC ACC AGG AGG CTG TGC AGC TTC AAT            962
282 Arg Val Pro Arg Asp Lys Leu Ala Ile Thr Arg Arg Leu Cys Ser Phe Asn               301
963 ATC AAG ATC ACC AAG AAT AAT GAG CCA CCA TGC TGT CGC GAT GAG TTC GCC CGC ATC TAC  1022
302 Ile Lys Ile Thr Lys Asn Asn Glu Pro Pro Cys Cys Arg Asp Glu Phe Ala Arg Ile Tyr   321
```

```
1023 ATC GTC CTG AAG GGC AAC CCC CCT CGC CTG CAG TCC AAC ATC CAG TAC ATC ACT CGC TTC  1082
 322 Ile Val Leu Lys Gly Asn Pro Pro Arg Leu Gln Ser Asn Ile Gln Tyr Ile Thr Arg Phe   341
1083 TGC AAC CCC AGC CGG CTC ATG GGC GAG TAC TTC TAC AAC CTG TGC TGT 1142
 342 Cys Asn Pro Ser Arg Leu Met Gly Glu Tyr Phe Tyr Asn Leu Cys Cys  361
1143 GCT GTG GCT TTC ATT GAG GCT TTG TCT TTA GAC GCC CAG TCT TTA AGT CAG GAG GAT TTT 1202
 362 Ala Val Ala Phe Ile Glu Ala Leu Ser Leu Asp Ala Gln Ser Leu Ser Gln Glu Asp Phe   381
1203 GAC CGG TAC ATG TCT GGC ACA TCC CCC AGG AAG CAG GAG TCT GAG AGT TGG CCC CCG 1262
 382 Asp Arg Tyr Met Ser Gly Thr Ser Pro Arg Lys Gln Glu Ser Glu Trp Pro Pro   401
1263 GAG GCC TGC TTA GGT GTG AAG CAA ATG TTG GAC CTC CTG TCT CAG TTG AAT 1322
 402 Glu Ala Cys Leu Gly Val Lys Gln Met Leu Asp Leu Leu Ser Gln Leu Asn   421
1323 GAA CGG CAA GAA AGG ATC AAC GAA GCC CTT AAA AAG CTT TTA ATA GAC TGG 1382
 422 Glu Arg Gln Glu Arg Ile Asn Glu Ala Leu Lys Lys Leu Leu Ile Asp Trp   441
1383 GAA GAC GGG ATT GCC AAG GAA GTT CAA GAA CTT GAG AAA TAC CCA CTG GAG ATT AAG 1442
 442 Glu Asp Gly Ile Ala Lys Glu Val Gln Glu Leu Glu Lys Tyr Pro Leu Glu Ile Lys   461
1443 ACA GAC CCG AAC CAA CCC TTA GCA GCC ATC GAC TCT GAG AAC GAC AAG CTC CCT 1502
 462 Thr Asp Pro Asn Gln Pro Leu Ala Ala Ile Asp Ser Glu Asn Asp Lys Leu Pro   481
1503 CCC CCT CTG CAG CCT CAG GTG TAC GCA GGG TGACGGCCCTGTTTATTGGGGCTGGTTTCTGGGAGCTG 1571
 482 Pro Pro Leu Gln Pro Gln Val Tyr Ala Gly ***   491
1572 CTGCGTTCCACTGTTCAGGTCCGGAATATGAACTGACTGCTTAAAGTTTCAAAGTGTTTTAGGTACAGATTTAGGGAT 1650
1651 TGGTTATTCTCTTTTTTCTTCTGTCGCTTCTTCTGCCTTAGTAAATAAATGTACTATTATTTGAGCTGGTGGAGTAGG 1729
1730 TTTGTGTGTGAATTCTGAATTGTCCTGCCTGATTCCCATGGGCTTCCTCTGTGTAGACACTGTGTTGTGGT 1808
1809 TTTGGCAAACACTGCCTTTTAAAGGATAAAAACAGATGCTATATAAAGATGCTATGTGTAGAATGAATTCTATGTTCCCACACT 1887
1888 CCCCAGTGTGAAATAATTTGTAATTGTAAAGATAAATGTAATAAGTAATATATGTAAAATTGTAAATATGT 1966
2967 AAAAAAAAACACATAGGGCTGGGAGGGTGTCTCAGCGTGCCATGCATTTCATGAGCTGATTTGTTTTTTTTTTTT 2045
2046 TAGGTGAAAATGAAATTTATTGAACATTGGCACTAACTGCCCTAACTGCCCTAACTGCCTTTAGCGCCTAACTGCCCTAACTGCCCTTTAGCGCCTAAGAATCTAAAGA 2124
2125 ATTTGAGCTTTAAACAGGACATACAGAATTATTCTGGGACCCTGGGTGGTGCTCAGTCAGTAAAGTGCTCTCCTATACTGAT 2203
2204 CAACTTTTAGGTCACATACAGAATTATTCTGGGACCCTGGGTGAAAAGCTGGTGACACTCACTTGGGACAGCTCTGCTGGA 2282
2283 GTGAGGACCTGAGTCCTGGGGGCAGGGCATCGTCAATGAGAGACACCTCGTGTAAGCAAACAAATCAAGATGGACGGCTCCT 2361
2362 GCCAGAGTTCCTGGGGGCAGGGCATCGTCAATGAGAGACACCTCGTGTAAGCAAACAAATCAAGATGGACGGCTCCT 2440
2441 GAGAAATGATAGCCAAGGATGCCCCTGCTGATTAGTACAGTTGACTTGGAACTGTCCTGTGCTTGCCTGTGCTTGCAGCTGTCCTTTCCAGCTTCCTTTCCTGTGCCTTCCTGTGCTTGCAGCTTCCTTTCCTGTGCTTGCAGCTGTACATGTAGC 2519
2520 ACACACACAGTGAACACACACAGTGCTGCTATTGCCTTTTATCTGAAATCGAAAAAAAAAAAAAAAAAA 2598
2599 AATAAACTTCCCCCACAGTGCTGTGGGGCTATTGCCTTTTATCTGAAATCGAAAAAAAAAAAAAAAAAA 2664
```

FIG. 3B

| | | | | | |
|---|---|---|---|---|---|
| Rin2 | 227 | ETTDDEKKDL | AIQKRIRALH | WVTPQMLCVP | VNEEIPEVSD MVVKAITDII |
| Vps9p | 157 | EHMKDLTNDD | TLLEKIRHYR | FISPIMLDIP | DTMPNARLNK FVHLASKELG |
| Rin1 | 155 | RLAADG-SLG | RLAEGLRLAR | AQGPGAFGSH | LSLPSPVE-- -LEQVRQKLL |
| JC265 | 182 | FHMADG-SWK | QLKENLQLVR | QRNPQELGVF | APTPDFVD-- -VEKIKVKFM |

| | | | | | |
|---|---|---|---|---|---|
| Rin2 | 277 | EMDSKRVPRD | KLACITRCSK | HIFNAIKITK | NEPASADDFL PTLIYIVLKG |
| Vps9p | 207 | KINRFKSPRD | KMVCVLNASK | VIFGLLKHTK | LEQNGADSFI PVLIYCILKG |
| Rin1 | 201 | QLVRTYSPSA | QVKRLLQACK | LLYMALRTQE | GEGSGADGFL PLLSLVLAHC |
| JC265 | 228 | TMQKMYSPEK | KVMLLLRVCK | LIYTVMENNS | GRMYGADDFL PVLTYVIAQC |

LL  CK LIY       GAD FL PVL

MOTIF I        MOTIF II

| | | | | | |
|---|---|---|---|---|---|
| Rin2 | 327 | NPPRLQSNIQ | YITRFCNPSR | LMTGEDGYYF | TNLCCAVAFI EKLDAQSL |
| Vps9p | 257 | QVRYLVSNVN | YIERFRSPDF | I-RGEEEYYL | SSLQAALNFI MSLTERSL |
| Rin1 | 251 | DLPELLLEAE | YMSELLEPSL | L-TGEGGYYL | TSLSASLALL SGLGQAHT |
| JC265 | 278 | DMLELDTEIE | YMMELLDPSL | L-HGEGGYYL | TSAYGALSLI KNFQEEQA |

GE YYL TS

MOTIF III

FIG. 4

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 2664 base pairs
      (B) TYPE: nucleic acid
      (C) STRANDEDNESS: single
      (D) TOPOLOGY: linear (ii) MOLECULE TYPE: Genomic DNA (ix) FEATURE:
      (A) NAME/KEY: Coding Sequence
      (B) LOCATION: 60...1532
      (D) OTHER INFORMATION:

(xi) SEQUENCE DESCRIPTION: SEQ ID NO:1:

```
GCACGAGGGG CGCTGGGAGC GGCGGTCGGA CGCCGGCGGA GCCGCGGAGC AGGAAGAAG        59

ATG AGC CTG AAG TCC GAA CGC AGG GGA ATT CAT GTG GAT CAA TCT GAG      107
Met Ser Leu Lys Ser Glu Arg Arg Gly Ile His Val Asp Gln Ser Glu
 1               5                  10                  15

CTC CTG TGC AAG AAA GGA TGC GGT TAC TAC GGC AAC CCT GCC TGG CAG      155
Leu Leu Cys Lys Lys Gly Cys Gly Tyr Tyr Gly Asn Pro Ala Trp Gln
            20                  25                  30
```

```
GGT TTC TGC TCC AAG TGC TGG AGG GAG GAG TAC CAC AAG GCC CGG CAG     203
Gly Phe Cys Ser Lys Cys Trp Arg Glu Glu Tyr His Lys Ala Arg Gln
         35                  40                  45

AGG CAG ATC CAA GAG GAC TGG GAA CTG GCA GAA CGA CTT CAG CGG GAG     251
Arg Gln Ile Gln Glu Asp Trp Glu Leu Ala Glu Arg Leu Gln Arg Glu
 50                  55                  60

GAG GAA GAG GCC TTC GCG AGC AGC CAG AGC AGC CAA GGA GCC CAG TCC     299
Glu Glu Glu Ala Phe Ala Ser Ser Gln Ser Ser Gln Gly Ala Gln Ser
 65                  70                  75                  80

CTC ACC TTC TCC AAG TTC GAG GAG AAG AAG ACC AAT GAG AAA ACC CGA     347
Leu Thr Phe Ser Lys Phe Glu Glu Lys Lys Thr Asn Glu Lys Thr Arg
                 85                  90                  95

AAA GTC ACC ACA GTG AAG AAG TTC TTC AGC GCC TCT TCC AGA GCT GGA     395
Lys Val Thr Thr Val Lys Lys Phe Phe Ser Ala Ser Ser Arg Ala Gly
                100                 105                 110

TCC AAG AAG GAA ATT CAG GAA GCC AAA GCT CCC AGT CCC TCC ATA AAC     443
Ser Lys Lys Glu Ile Gln Glu Ala Lys Ala Pro Ser Pro Ser Ile Asn
                    115                 120                 125

CGG CAA ACC AGC ATT GAG ACG GAC CGA GTG ACT AAG GAG TTC ATA GAC     491
Arg Gln Thr Ser Ile Glu Thr Asp Arg Val Thr Lys Glu Phe Ile Asp
130                 135                 140

TTT CTC AAG ACC TTC CAC AAG ACA GGC CAA GAA GTC TAT AAA CAG ACG     539
Phe Leu Lys Thr Phe His Lys Thr Gly Gln Glu Val Tyr Lys Gln Thr
145                 150                 155                 160

AAG ATG TTT TTG GAA GCA ATG CCT TAT AAA AGG GAT TTA AGC ATC GAG     587
Lys Met Phe Leu Glu Ala Met Pro Tyr Lys Arg Asp Leu Ser Ile Glu
                165                 170                 175

GAA CAG TCA GAA TGT ACT CAG GAC TTT TAC CAA AAT GTG GCT GAA AGA     635
Glu Gln Ser Glu Cys Thr Gln Asp Phe Tyr Gln Asn Val Ala Glu Arg
                180                 185                 190

ATG CAG ACC CGT GGG AAA GTG CCT CCA GAG AAA GTG GAG AAG ATA ATG     683
Met Gln Thr Arg Gly Lys Val Pro Pro Glu Lys Val Glu Lys Ile Met
                195                 200                 205

GAT CAG ATC GAA AAG CAC ATC ATG ACG CGT CTC TAT AAA TTT GTG TTC     731
Asp Gln Ile Glu Lys His Ile Met Thr Arg Leu Tyr Lys Phe Val Phe
210                 215                 220

TGC CCA GAG ACT ACT GAT GAT GAG AAG AAA GAT CTC GCC ATT CAA AAA     779
Cys Pro Glu Thr Thr Asp Asp Glu Lys Lys Asp Leu Ala Ile Gln Lys
225                 230                 235                 240

AGA ATC AGG GCC CTG CAC TGG GTA ACG CCT CAG ATG CTC TGT GTC CCT     827
Arg Ile Arg Ala Leu His Trp Val Thr Pro Gln Met Leu Cys Val Pro
                245                 250                 255

GTC AAT GAG GAA ATC CCT GAA GTG TCC GAC ATG GTG GTG AAA GCG ATC     875
Val Asn Glu Glu Ile Pro Glu Val Ser Asp Met Val Val Lys Ala Ile
                260                 265                 270

ACA GAC ATC ATT GAG ATG GAC TCA AAG CGT GTG CCT CGG GAC AAG CTG     923
Thr Asp Ile Ile Glu Met Asp Ser Lys Arg Val Pro Arg Asp Lys Leu
                275                 280                 285

GCC TGC ATC ACC AGG TGC AGC AAG CAC ATC TTC AAT GCC ATC AAG ATC     971
Ala Cys Ile Thr Arg Cys Ser Lys His Ile Phe Asn Ala Ile Lys Ile
290                 295                 300

ACC AAG AAT GAG CCA GCC TCT GCC GAT GAC TTC CTG CCC ACC CTG ATC    1019
Thr Lys Asn Glu Pro Ala Ser Ala Asp Asp Phe Leu Pro Thr Leu Ile
305                 310                 315                 320

TAC ATC GTC CTG AAG GGC AAC CCC CCT CGC CTG CAG TCC AAC ATC CAG    1067
Tyr Ile Val Leu Lys Gly Asn Pro Pro Arg Leu Gln Ser Asn Ile Gln
                325                 330                 335

TAC ATC ACT CGC TTC TGC AAC CCC AGC CGG CTC ATG ACG GGC GAG GAT    1115
Tyr Ile Thr Arg Phe Cys Asn Pro Ser Arg Leu Met Thr Gly Glu Asp
                340                 345                 350
```

| | | |
|---|---|---|
| GGC TAC TAC TTC ACC AAC CTG TGC TGT GCT GTG GCT TTC ATT GAG AAA<br>Gly Tyr Tyr Phe Thr Asn Leu Cys Cys Ala Val Ala Phe Ile Glu Lys<br>355                              360                        365 | 1163 |
| TTA GAC GCC CAG TCT TTG AAT TTA AGT CAG GAG GAT TTT GAC CGG TAC<br>Leu Asp Ala Gln Ser Leu Asn Leu Ser Gln Glu Asp Phe Asp Arg Tyr<br>370                              375                        380 | 1211 |
| ATG TCT GGC CAG ACA TCC CCC AGG AAG CAG GAG TCT GAG AGT TGG CCC<br>Met Ser Gly Gln Thr Ser Pro Arg Lys Gln Glu Ser Glu Ser Trp Pro<br>385                              390                        395                    400 | 1259 |
| CCG GAG GCC TGC TTA GGT GTG AAG CAA ATG TAT AAG AAC TTG GAC CTC<br>Pro Glu Ala Cys Leu Gly Val Lys Gln Met Tyr Lys Asn Leu Asp Leu<br>                          405                        410                        415 | 1307 |
| CTG TCT CAG TTG AAT GAA CGG CAA GAA AGG ATC ATG AAC GAA GCC AAG<br>Leu Ser Gln Leu Asn Glu Arg Gln Glu Arg Ile Met Asn Glu Ala Lys<br>                    420                        425                        430 | 1355 |
| AAA CTT GAA AAA GAC TTA ATA GAC TGG ACA GAC GGG ATT GCC AAG GAA<br>Lys Leu Glu Lys Asp Leu Ile Asp Trp Thr Asp Gly Ile Ala Lys Glu<br>                    435                        440                        445 | 1403 |
| GTT CAA GAC ATT GTT GAG AAA TAC CCA CTG GAG ATT AAG CCC CCG AAC<br>Val Gln Asp Ile Val Glu Lys Tyr Pro Leu Glu Ile Lys Pro Pro Asn<br>450                              455                        460 | 1451 |
| CAA CCC TTA GCA GCC ATC GAC TCT GAG AAT GTG GAG AAC GAC AAG CTC<br>Gln Pro Leu Ala Ala Ile Asp Ser Glu Asn Val Glu Asn Asp Lys Leu<br>465                              470                        475                    480 | 1499 |
| CCT CCC CCT CTG CAG CCT CAG GTG TAC GCA GGG TGACGGCCCT GTTTATTTGG<br>Pro Pro Pro Leu Gln Pro Gln Val Tyr Ala Gly<br>                        485                        490 | 1552 |
| GGCTGGTTTC TGGGAGCTGC TGCGTTCCAC TGTTCAGGTC CGGAATATGA ACTGACTGCT | 1612 |
| TAAAGTTTCA AAGTGTTTTT AGGTACAGAT TTAGGGATTG GTTATTCTCT TTTTTCTTCT | 1672 |
| CTAGCGGGGA AGCTTAGTAA ATAATAATGT ACTATTTATT TGAGCTGGTG GAGTAGGTTT | 1732 |
| GTGTGAATTC TGTGTCGCTC TTTTATGTCC TGCCTGATTT CCCATGGGCT TCCTCTGTGT | 1792 |
| AGACACTGTT GTTGGTTTTG GGCAAACACT GCCTTTTAAA GGATAAAACA GATGCTATAA | 1852 |
| AGTCTATGTT GAAATGAATT CTATGTTCCC ACACTCCCCC AGTGTGAAAT AATTTTGTAA | 1912 |
| TTGTAAAGAT AGAAGATAAT GTTAATAAGT AAATATGTAA AATTGTAAAT ATGTAAAAAA | 1972 |
| AAAACACATA GGGCTGGGGA GGGGTGTCTC AGCGTGCATG GCATTTCATG AGCTGATGTT | 2032 |
| TTTTTTTTTT TTTTAGGTGA AAATGAAATT TATTGAATGT TTGCCTTTAG CGCCATTTTA | 2092 |
| TATGGTTTGT CCCACTAAAA AGAATCTAAA GAATTTGAGC TTTAACAGGA CATTGGCACT | 2152 |
| AACTGCCCTA ACTTGAGATT CTTTCTGGTA CATGTGAAGA AGTTGTAACG CCAACTTTTA | 2212 |
| GGTCACATAC AGAATTATTC TGGGACCCTG GGGTGGTGGC TCAGTCAGTA AAGTGCTCTC | 2272 |
| CTATACTGAT GTGAGGACCT GAGCTCCCTG TCCGGCCCCG GGTGAAAAGC TGGGCATGGT | 2332 |
| GACACTCACT TGGGACAGCT CTGCTGGGAG CCAGAGTTCC TGGGGCAGGG GGCATCGCTG | 2392 |
| TCAATGAGAC ACCTCGTGTA AGCAAACAAA TCAAGATGGA CGGCTCCTGA GAAATGATAG | 2452 |
| CCAAGGATGC CCTCTGGCCT CCACATGGCC ACATATGTGC CTGTGTACCT CTACATACAT | 2512 |
| GTGTAGCACA CACACATGAA CACACAGTTG CTGATTAGTA CAGTTGACTT GGAACTGTGC | 2572 |
| TTGCAGCTTC CTTTCCCTGT TTATCCAATA AACTTCCCCC ACAGTGCTGT GGGGCTATTG | 2632 |
| CCTTTTTTAT CTGAAAAAAA AAAAAAAAA AA | 2664 |

(2) INFORMATION FOR SEQ ID NO:2:

(i) SEQUENCE CHARACTERISTICS:
        (A) LENGTH: 491 amino acids (B) TYPE: amino acid
(C) STRANDEDNESS: single
(D) TOPOLOGY: linear (ii) MOLECULE TYPE: protein (v) FRAGMENT TYPE: internal (xi) SEQUENCE DESCRIPTION: SEQ ID NO:2:

Met Ser Leu Lys Ser Glu Arg Arg Gly Ile His Val Asp Gln Ser Glu
1               5                   10                  15

Leu Leu Cys Lys Lys Gly Cys Gly Tyr Tyr Gly Asn Pro Ala Trp Gln
                20                  25                  30

Gly Phe Cys Ser Lys Cys Trp Arg Glu Glu Tyr His Lys Ala Arg Gln
            35                  40                  45

Arg Gln Ile Gln Glu Asp Trp Glu Leu Ala Glu Arg Leu Gln Arg Glu
        50                  55                  60

Glu Glu Glu Ala Phe Ala Ser Ser Gln Ser Ser Gln Gly Ala Gln Ser
65                  70                  75                  80

Leu Thr Phe Ser Lys Phe Glu Glu Lys Lys Thr Asn Glu Lys Thr Arg
                85                  90                  95

Lys Val Thr Thr Val Lys Lys Phe Phe Ser Ala Ser Ser Arg Ala Gly
                100                 105                 110

Ser Lys Lys Glu Ile Gln Glu Ala Lys Ala Pro Ser Pro Ser Ile Asn
            115                 120                 125

Arg Gln Thr Ser Ile Glu Thr Asp Arg Val Thr Lys Glu Phe Ile Asp
        130                 135                 140

Phe Leu Lys Thr Phe His Lys Thr Gly Gln Glu Val Tyr Lys Gln Thr
145                 150                 155                 160

Lys Met Phe Leu Glu Ala Met Pro Tyr Lys Arg Asp Leu Ser Ile Glu
                165                 170                 175

Glu Gln Ser Glu Cys Thr Gln Asp Phe Tyr Gln Asn Val Ala Glu Arg
            180                 185                 190

Met Gln Thr Arg Gly Lys Val Pro Pro Glu Lys Val Glu Lys Ile Met
        195                 200                 205

Asp Gln Ile Glu Lys His Ile Met Thr Arg Leu Tyr Lys Phe Val Phe
210                 215                 220

Cys Pro Glu Thr Thr Asp Asp Glu Lys Lys Asp Leu Ala Ile Gln Lys
225                 230                 235                 240

Arg Ile Arg Ala Leu His Trp Val Thr Pro Gln Met Leu Cys Val Pro
                245                 250                 255

Val Asn Glu Glu Ile Pro Glu Val Ser Asp Met Val Val Lys Ala Ile
            260                 265                 270

Thr Asp Ile Ile Glu Met Asp Ser Lys Arg Val Pro Arg Asp Lys Leu
        275                 280                 285

Ala Cys Ile Thr Arg Cys Ser Lys His Ile Phe Asn Ala Ile Lys Ile
290                 295                 300

Thr Lys Asn Glu Pro Ala Ser Ala Asp Asp Phe Leu Pro Thr Leu Ile
305                 310                 315                 320

Tyr Ile Val Leu Lys Gly Asn Pro Pro Arg Leu Gln Ser Asn Ile Gln
                325                 330                 335

Tyr Ile Thr Arg Phe Cys Asn Pro Ser Arg Leu Met Thr Gly Glu Asp
            340                 345                 350

Gly Tyr Tyr Phe Thr Asn Leu Cys Cys Ala Val Ala Phe Ile Glu Lys
        355                 360                 365

```
Leu Asp Ala Gln Ser Leu Asn Leu Ser Gln Glu Asp Phe Asp Arg Tyr
        370                 375                 380

Met Ser Gly Gln Thr Ser Pro Arg Lys Gln Glu Ser Glu Ser Trp Pro
385                 390                 395                 400

Pro Glu Ala Cys Leu Gly Val Lys Gln Met Tyr Lys Asn Leu Asp Leu
                405                 410                 415

Leu Ser Gln Leu Asn Glu Arg Gln Glu Arg Ile Met Asn Glu Ala Lys
            420                 425                 430

Lys Leu Glu Lys Asp Leu Ile Asp Trp Thr Asp Gly Ile Ala Lys Glu
        435                 440                 445

Val Gln Asp Ile Val Glu Lys Tyr Pro Leu Glu Ile Lys Pro Pro Asn
    450                 455                 460

Gln Pro Leu Ala Ala Ile Asp Ser Glu Asn Val Glu Asn Asp Lys Leu
465                 470                 475                 480

Pro Pro Pro Leu Gln Pro Gln Val Tyr Ala Gly
                485                 490
```

(2) INFORMATION FOR SEQ ID NO:3:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:3:

AGCCAGCGAA                                                              10

(2) INFORMATION FOR SEQ ID NO:4:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:4:

GACCGCTTGT                                                               10

(2) INFORMATION FOR SEQ ID NO:5:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:5:

AGGTGACCGT                                                              10

(2) INFORMATION FOR SEQ ID NO:6:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:6:

GGTACTCCAC                                                                10

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:7:

GTTGCGATCC                                                                10

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Ser Ala Asp Asp Phe Leu Pro Thr Leu
 1               5

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Gly Ala Asp Xaa Phe Leu Pro Val Leu
 1               5

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Gly Glu Asp Gly Tyr Tyr Phe Thr Asn
 1               5

(2) INFORMATION FOR SEQ ID NO:11:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Gly Glu Xaa Xaa Tyr Tyr Leu Thr Ser
1               5
```

(2) INFORMATION FOR SEQ ID NO:12:

(i) SEQUENCE CHARACTERISTICS:
        (A) LENGTH: 148 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:12:

```
Glu Thr Thr Asp Asp Glu Lys Lys Asp Leu Ala Ile Gln Lys Arg Ile
1               5                   10                  15

Arg Ala Leu His Trp Val Thr Pro Gln Met Leu Cys Val Pro Val Asn
                20                  25                  30

Glu Glu Ile Pro Glu Val Ser Asp Met Val Val Lys Ala Ile Thr Asp
            35                  40                  45

Ile Ile Glu Met Asp Ser Lys Arg Val Pro Arg Asp Lys Leu Ala Cys
50                  55                  60

Ile Thr Arg Cys Ser Lys His Ile Phe Asn Ala Ile Lys Ile Thr Lys
65                  70                  75                  80

Asn Glu Pro Ala Ser Ala Asp Asp Phe Leu Pro Thr Leu Ile Tyr Ile
                85                  90                  95

Val Leu Lys Gly Asn Pro Pro Arg Leu Gln Ser Asn Ile Gln Tyr Ile
                100                 105                 110

Thr Arg Phe Cys Asn Pro Ser Arg Leu Met Thr Gly Glu Asp Gly Tyr
                115                 120                 125

Tyr Phe Thr Asn Leu Cys Cys Ala Val Ala Phe Ile Glu Lys Leu Asp
        130                 135                 140

Ala Gln Ser Leu
145
```

(2) INFORMATION FOR SEQ ID NO:13:

(i) SEQUENCE CHARACTERISTICS:
        (A) LENGTH: 147 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:13:

```
Glu His Met Lys Asp Leu Thr Asn Asp Asp Thr Leu Leu Glu Lys Ile
1               5                   10                  15

Arg His Tyr Arg Phe Ile Ser Pro Ile Met Leu Asp Ile Pro Asp Thr
                20                  25                  30

Met Pro Asn Ala Arg Leu Asn Lys Phe Val His Leu Ala Ser Lys Glu
            35                  40                  45

Leu Gly Lys Ile Asn Arg Phe Ser Pro Arg Asp Lys Met Val Cys
        50                  55                  60

Val Leu Asn Ala Ser Lys Val Ile Phe Gly Leu Leu Lys His Thr Lys
65                  70                  75                  80

Leu Glu Gln Asn Gly Ala Asp Ser Phe Ile Pro Val Leu Ile Tyr Cys
                85                  90                  95

Ile Leu Lys Gly Gln Val Arg Tyr Leu Val Ser Asn Val Asn Tyr Ile
                100                 105                 110
```

```
Glu Arg Phe Arg Ser Pro Asp Phe Ile Arg Gly Glu Glu Tyr Tyr
        115                 120                 125

Leu Ser Ser Leu Gln Ala Ala Leu Asn Phe Ile Met Ser Leu Thr Glu
130             135                 140

Arg Ser Leu
145
```

(2) INFORMATION FOR SEQ ID NO:14:

(i) SEQUENCE CHARACTERISTICS:
        (A) LENGTH: 143 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:14:

```
Arg Leu Ala Ala Asp Gly Ser Leu Gly Arg Leu Ala Glu Gly Leu Arg
1               5                   10                  15

Leu Ala Arg Ala Gln Gly Pro Gly Ala Phe Gly Ser His Leu Ser Leu
        20                  25                  30

Pro Ser Pro Val Glu Leu Glu Gln Val Arg Gln Lys Leu Leu Gln Leu
        35                  40                  45

Val Arg Thr Tyr Ser Pro Ser Ala Gln Val Lys Arg Leu Leu Gln Ala
50                  55                  60

Cys Lys Leu Leu Tyr Met Ala Leu Arg Thr Gln Glu Gly Glu Gly Ser
65                  70                  75                  80

Gly Ala Asp Gly Phe Leu Pro Leu Leu Ser Leu Val Leu Ala His Cys
                85                  90                  95

Asp Leu Pro Glu Leu Leu Glu Ala Glu Tyr Met Ser Glu Leu Leu
                100                 105                 110

Glu Pro Ser Leu Leu Thr Gly Gly Gly Tyr Tyr Leu Thr Ser Leu
        115                 120                 125

Ser Ala Ser Leu Ala Leu Leu Ser Gly Leu Gly Gln Ala His Thr
130                 135                 140
```

(2) INFORMATION FOR SEQ ID NO:15:

(i) SEQUENCE CHARACTERISTICS:
        (A) LENGTH: 143 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:15:

```
Phe His Met Ala Asp Gly Ser Trp Lys Gln Leu Lys Glu Asn Leu Gln
1               5                   10                  15

Leu Val Arg Gln Arg Asn Pro Gln Glu Leu Gly Val Phe Ala Pro Thr
        20                  25                  30

Pro Asp Phe Val Asp Val Glu Lys Ile Lys Val Lys Phe Met Thr Met
        35                  40                  45

Gln Lys Met Tyr Ser Pro Glu Lys Lys Val Met Leu Leu Leu Arg Val
50                  55                  60

Cys Lys Leu Ile Tyr Thr Val Met Glu Asn Asn Ser Gly Arg Met Tyr
65                  70                  75                  80

Gly Ala Asp Asp Phe Leu Pro Val Leu Thr Tyr Val Ile Ala Gln Cys
                85                  90                  95
```

-continued

```
Asp Met Leu Glu Leu Asp Thr Glu Ile Glu Tyr Met Met Glu Leu Leu
        100                 105                 110

Asp Pro Ser Leu Leu His Gly Glu Gly Gly Tyr Tyr Leu Thr Ser Ala
        115                 120                 125

Tyr Gly Ala Leu Ser Leu Ile Lys Asn Phe Gln Glu Glu Gln Ala
    130                 135                 140
```

RIN2, A NOVEL INHIBITOR OF RAS-MEDIATED SIGNALING

RELATED APPLICATIONS

The present application claims the benefit of U.S. Provisional Application Serial No. 60/058,520, entitled "Rin2, a Novel Inhibitor of Ras-mediated Signaling" by See-Ying Tam, Mindy Tsai, and Stephen J. Galli, filed Sep. 11, 1997. The teachings of the prior application are incorporated herein in their entirety.

GOVERNMENT FUNDING

Work described herein was supported by grants CA72074 and AI23990 from the National Institutes of Health. The United States government has certain rights in the invention.

BACKGROUND OF THE INVENTION

The Ras family of small guanine-nucleotide binding proteins plays a pivotal role in many intracellular signal transduction pathways, including those which regulate cellular growth and differentiation and those which contribute to cell activation (Bourne et al., *Nature* 348:125–132 (1990); Marshall, *FASEB J.* 9:1311–1318 (1995)). Moreover, many different receptors expressed on the surface of diverse cell types can result in the activation of signal transduction pathways that are importantly influenced by Ras, and these pathways in turn determine whether, and to what extent, these cells respond to such cell surface receptor-dependent activation by proliferating, differentiating (i.e., developing new functional characteristics), and/or expressing specific functions (FIG. 1).

Depending on the circumstances, these "down-stream" consequences of the activation of Ras-dependent signal transduction pathways can have either adaptive (physiological) or maladaptive (pathological) consequences. For example, controlled Ras-dependent cellular proliferation is required for wound healing, whereas poorly regulated Ras-dependent cellular proliferation can result in the development of cancer and other neoplasms. Similarly, appropriate Ras-dependent cell secretion of histamine, serotonin, cytokines and other mediators can be important for host defense against parasites and other pathogens, whereas the inappropriate activation of these same pathways, for example, by a reaction to a bee-sting in patients who are allergic to components of bee venom, can lead to fatal anaphylaxis. Thus, Ras represents a major regulator of many of the most fundamental biological processes involved in both health and disease.

The mechanism by which Ras regulates such processes, through interactions with other intracellular molecules, is quite complex. Ras proteins are membrane-associated proteins that cycle between an active GTP-bound form and an inactive GDP-bound form. As illustrated in FIG. 1, evidence is accumulating for the existence of many different classes of positive or negative regulators of Ras and positive or negative Ras signaling effectors, all of which, by definition, are thought to interact directly with the active GTP-bound form of Ras to influence cellular signaling for growth, differentiation and expression of function (Boguski and McCormick, *Nature* 366:643–654 (1993); Marshall, *FASEB J.* 9:1311–1318 (1995); Marshall, *Curr. Opin. Cell Biol* 8:197–204 (1996)). For example, some of the best-characterized Ras regulators include the GTPase activating proteins (GAPs) and guanine nucleotide exchange factors (Boguski and McCormick, *Nature* 366:643–654 (1993)).

The GAPs represent a family of Ras-binding proteins which stimulate the intrinsic rate of Ras GTP hydrolysis and thus negatively regulate the Ras-induced signaling by accelerating the conversion of active GTP-bound form of Ras to the inactive GDP-bound form. Recent studies have identified several GAPs specific for Ras proteins, which include p120-Ras GAP, neurofibromin (the protein encoded by the neurofibromatosis type 1 (NF1) gene), Gap1, Ral-GDS, Rsbs 1, 2, and 4, Rin1, MEKK-1, and phosphatidylinositol-3-OH kinase (PI3K) (Boguski and McCormick, *Nature* 366:643–654 (1993)).

In contrast to Ras regulators, which function primarily by influencing the amount of Ras which is in the GTP-bound active, as opposed to the GDP-bound inactive, form, Ras effectors are thought to influence the ability of active, GTP-bound Ras to initiate signaling (FIG. 1). In the case of many Ras-interacting proteins which can influence the intensity of Ras-dependent signaling, it is not yet clear to what extent they function as effectors as opposed to regulators; such proteins can therefore be called Ras regulators/effectors (Boguski and McCormick, *Nature* 366:643–54 (1993); Han and Colicelli, *Mol. Cell. Biol.* 15:1318–1323 (1995); Marshall, *FASEB J.* 9:1311–1318 (1995); Marshall, *Curr. Opin. Cell. Biol.* 8:197–204 (1996)).

A large number of cell types demonstrate the importance of Ras in critical cell signaling events. For example, mast cells are important effector cells in IgE-dependent immune responses and allergic diseases (Galli, *New Engl. J. Med.* 328:257–265 (1993)), and mast cells also contribute to host defense against parasites and bacteria (Echtenacher et al., *Nature* 381:75–77 (1996); Malaviya et al., *Nature* 381:77–80 (1996); Galli and Wershil, *Nature* 381:21–22 (1996)). Mast cells reside in virtually all vascularized tissues and express on their surface the high affinity receptor for IgE (FcεRI). Aggregation of FcεRI in mast cells by the interaction of receptor-bound IgE with specific multivalent antigen triggers the functional activation of mast cells, which results in the release of a spectrum of biologically active mediators (Ravetch and Kinet, *Ann. Rev. Immunol.* 9:457–492 (1991); Galli, *New Engl. J. Med.* 328:257–265 (1993); Beaven and Metzger, *Immunol. Today* 14:222–226 (1993)). Thus, mast cells activated by FcεRI-dependent mechanisms undergo degranulation, resulting in the release of preformed mediators, such as serotonin (5-HT) and/or histamine, the metabolism of arachidonic acid, leading to the release of newly synthesized lipid mediators, and the transcription, translation and secretion of several cytokines (Gordon et al., *Immunol. Today* 11:458–464 (1990); Galli, *New Engl. J. Med.* 328:257–265 (1993); Paul et al., *Adv. Immunol.* 53:1–29 (1993)).

Knowledge of the signaling pathways which result in the FcεRI-dependent secretion of mast cell mediators is increasing. In mast cells and basophils, a type of circulating leukocyte which shates many biochemical and functional characteristics with mast cells (Galli, *New Engl. J. Med.* 328:257–265 (1993)), the FcεRI receptor is a tetrameric complex comprised of a single 45 kDa α chain, which binds the Fc portion of IgE, a single 30 kDa β chain, and a homodimer of two 10 kDa γ chains (Ravetch and Kinet, *Ann. Rev. Immunol.* 9:457–492 (1991); Beaven and Metzger, *Immunol. Today* 14:222–226 (1993)). The β and γ chains contain immunoreceptor tyrosine-based activation motifs (ITAM) which couple the receptor to the src family of protein tyrosine kinases (PTK) p56lyn and p72syk (Beaven and Baumgartner, *Curr. Opin. Immunol.* 8:766–772 (1996)). The FcεRI-dependent activation of these PTKs in turn activates various downstream effector pathways, including those involving PLCγ1 and the MAP kinase pathway (Beaven and Baumgartner, *Curr. Opin. Immunol.* 8:766–772 (1996)).

Recent studies have shown that the crosslinking of FcϵRI in mast cells by IgE and specific antigen also results in the activation of Ras and of the associated Shc-Grb2-Sos pathway, which precedes Ras activation, and that the activation of this pathway is dependent on Syk (Jabril-Cuenod et al., *J. Biol. Chem.* 271:16268–16272 (1996)). These results suggest that in FcϵRI-activated mast cells, as in T cells and B cells (the major types of lymphocytes responsible for cellular and humoral immunity) which have been activated via the T cell receptor or B cell receptor, respectively, the Shc-Grb2-Sos pathway can activate the MAP kinase pathway via the activation of Ras.

An effector pathway of Ras mediated by the Raf-1/Erk-activating kinases (MEKs)/Erk-MAP kinases cascade has been well-characterized in numerous systems (Treisman, *Curr. Opin. Cell Biol.* 8:205–215 (1996)), and this Ras-mediated pathway is important in the mast cell activation and mediator secretion that is induced by IgE- and antigen-dependent aggregation of FcϵRI in these cells (Tsai et al., *Eur. J. Immunol.* 23:3286–3291 (1993); Offermanns et al., *J. Immunol.* 152:250–261 (1994); Hirasawa et al., *J. Immunol.* 154:5391–5402 (1995)). In addition, recent studies with rat RBL2H3 mast cells have shown that the FcϵRI induction of Ras activation leads to transcriptional activation mediated by the transcription factors Elk-1 and the nuclear factor of activated T cells (NFAT) (Turner and Cantrell, *J. Exp. Med.* 185:43–53 (1997)). These Ras-dependent signaling pathways in mast cells appear to be complex. Thus, activation of the Raf-1/MEK/Erk cascade appears to be necessary and sufficient for the activation of Elk-1 activity in mast cells. However, the induction of NFAT by FcϵRI in mast cells is also mediated in part by Rac-1, which is a putative Ras effector and a member of the Rho family of GTP binding proteins (Turner and Cantrell, *J. Exp. Med.* 185:43–53 (1997)). Thus, the specific signaling pathways involved in FcϵRI-mediated mast cell activation are still unclear.

SUMMARY OF THE INVENTION

As described herein, mRNA differential display was used to identify the cDNA for a novel gene, rin2. As also described herein, expression of rin2 was shown to be rapidly increased in mouse mast cells activated through FcϵRI. Transfection of mouse mast cells with an antisense rin2 expression vector, which resulted in antisense inhibition of Rin2 expression, potentiated the Ras-mediated intracellular signaling responses that were induced by FcϵRI aggregation, such as the induction of c-fos expression and the activation of Erk-MAP kinase activity. In addition, antisense inhibition of rin2 expression in mouse mast cells significantly enhanced the amounts of preformed mediator (serotonin) and cytokine (IL-6) released from these cells upon FcϵRI-dependent stimulation, suggesting that Rin2 exerts its effects by down-regulating the functional responses elicited by FcϵRI aggregation in mast cells. These results support the role of Rin2 as a novel negative regulator/effector of Ras in mast cells.

Moreover, as also described herein, expression of rin2 is also increased in mast cells stimulated via activation of their major growth factor receptor (i.e., c-kit), in PC12 adrenal pheochromocytoma cells activated via the receptor for nerve growth factor (NGF) (i.e., TrkA), and in T cells activated via the T cell receptor (TCR). These findings support the role of Rin2 as a novel general negative regulator/effector of Ras and Ras-dependent signaling pathways in diverse cell types which have been activated via distinct cell surface receptors (FIG. 2). In addition, the enhancement or inhibition of Rin2 expression or function, in certain settings, resulting in the reduction or enhancement, respectively, of Ras-dependent siganling in these settings, may have benefit in diverse clinical problems, some examples of which are shown in FIG. 2.

Accordingly, this invention pertains to isolated Rin2 protein, which down-regulates the functional responses elicited by Ras-dependent signaling pathways. In one embodiment, Rin2 down-regulates the functional responses elicited by FcϵRI aggregation in mast cells (e.g., mammalian mast cells), including down-regulating the amounts of preformed mediator (serotonin) and cytokine (IL-6) released from these cells upon FcϵRI-dependent stimulation. In another embodiment, Rin2 down-regulates functional responses in mast cells stimulated via activation of their major growth factor receptor (i.e., c-kit). In another embodiment, Rin2 inhibits cell proliferation in PC12 adrenal pheochromocytoma cells stimulated through the nerve growth factor receptor (i.e., TrkA). In a further embodiment, Rin2 inhibits functional responses in T cells activated through the T cell receptor.

In one embodiment, isolated Rin2 protein has the amino acid sequence of SEQ ID NO: 2. In one embodiment, the Rin2 protein is a portion of SEQ ID NO: 2 which is sufficient for Rin2 activity, e.g., binding or enzymatic activity. Also included within the meaning of Rin2 protein or polypeptide are polypeptides which are less than the amino acid sequence of SEQ ID NO: 2 and have Rin2 activity, as well as proteins whose amino acid sequence is substantially similar to that of SEQ ID NO: 2 and have Rin2 activity.

In another embodiment, Rin2 protein is a derivative possessing substantial sequence identity with the endogenous Rin2 protein. In particular embodiments, the Rin2 protein is purified to homogeneity or is substantially free of other proteins.

The invention also pertains to an isolated nucleic acid molecule or nucleotide sequence (rin2) which encodes Rin2 protein or polypeptide, or a portion of SEQ ID NO: 2 which is sufficient for Rin2 activity. In one embodiment, the encoded Rin2 protein is a derivative possessing substantial sequence identity with the endogenous Rin2 protein. In a particular embodiment, the isolated nucleic acid molecule encodes Rin2 protein with the same amino acid sequence as endogenous Rin2 protein. In another embodiment, the isolated nucleic acid molecule has the same nucleotide sequence as the endogenous gene encoding Rin2 protein. In one embodiment, the isolated nucleic acid molecule has the nucleotide sequence of SEQ ID NO: 1.

The invention also relates to DNA constructs comprising the nucleic acid molecules described herein, operatively linked to a regulatory sequence, and to recombinant host cells, such as bacterial cells, fungal cells, plant cells, insect cells and mammalian cells, comprising the nucleic acid molecules described herein operatively linked to a regulatory sequence. The invention also relates to a method for preparing a Rin2 polypeptide, comprising culturing a recombinant host cell described herein.

The invention also pertains to an antibody, or an antigen-binding fragment thereof, which selectively binds to Rin2 protein, or a portion of SEQ ID NO: 2 which is sufficient for Rin2 activity; in a particular embodiment, the antibody is a monoclonal antibody. The invention also relates to a method for assaying the presence of Rin2 protein in a cell, e.g., in a tissue sample, comprising contacting said cell with an antibody which specifically binds to Rin2 protein.

The present invention also relates to an assay for identifying agents which alter the activity of Rin2 protein. For example, a cell population, e.g., a mast cell population, containing Rin2 protein can be activated with a stimulus which activates at least one Ras-dependent pathway in the cell in the presence of an agent to be tested, and the level of Rin2 activity can be assessed.

The invention further relates to methods of inhibiting the functional responses (e.g., proliferation, functional activation) elicited by activation of Ras-dependent signaling pathways in cells, comprising contacting the cells with an agent which enhances or mimics the activity of Rin2 protein. The invention also relates to a method of treating a mammal in need thereof to inhibit functional responses elicited by activation of Ras-dependent signaling pathways, comprising administering to a mammal an agent which enhances or mimics the activity of Rin2 protein.

The invention further relates to methods of inhibiting the functional responses elicited by FcεRI aggregation, particularly in mast cells, comprising contacting a mast cell population with an agent which enhances or mimics the activity of Rin2 protein. The invention relates to a method of treating a mammal in need thereof to inhibit the functional response elicited by FcεRI aggregation, comprising administering to a mammal an agent which enhances the activity of Rin2 protein. For example, the invention relates to methods of inhibiting IgE and antigen-dependent release of mediators from mast cells. Such methods can be used to inhibit mediator release from mast cells and other effector cells that express FcεRI, such as basophils, monocytes/macrophages, dendritic cells, Langerhans' cells and eosinophils, thereby ameliorating disorders such as asthma and allergic diseases (e.g., hay fever and atopic eczema).

The invention further relates to methods of enhancing functional responses (e.g., proliferation, functional activation) elicited by activation of Ras-dependent signaling pathways in cells, comprising contacting the cells with an agent which inhibits the activity of Rin2 protein. The invention also relates to a method of treating a mammal in need thereof to enhance functional responses elicited by activation of Ras-dependent signaling pathways, comprising administering to a mammal an agent which inhibits the activity of Rin2 protein.

BRIEF DESCRIPTION OF THE DRAWINGS

FIG. 3 is the cDNA sequence (SEQ ID NO: 1) and the predicted amino acid sequence (SEQ ID NO: 2) of the SY-A clone (Rin2). The predicted open reading frame begins at nucleotide 60 and ends at nucleotide 1535.

FIG. 4 shows an amino acid sequence alignment of the portion of Rin2 protein disclosed herein which exhibits the highest level of sequence similarity with known members of a GTPase-binding protein family. Specifically, the figure shows an alignment of the amino acid sequence corresponding to positions 227–374 of Rin2 (SEQ ID NO: 12), with the GTPase binding homology (GBH) domains of Vps9p (SEQ ID NO: 13), Rin1 (SEQ ID NO: 14), and JC265 (SEQ ID NO: 15). The GBH domains of Vps9p, Rin1, and JC265 and the GBH motifs I, II, and III illustrated here represent those described in Burd et al. (*Mol. Cell. Biol.* 16:2369–2377 (1996)). Proteins are identified on the left, and the position of the amino acid on each line is indicated. Identical amino acids or conservative substitutions present in three of four proteins are shaded. Conservative substitutions for the alignment were assigned as follows: V, L, I, and M; K, R, and H; F, Y, and W; D and E; N and Q; S and T; and G and A.

FIG. 7A illustrates the kinetics of IL-6 release induced by FcεRI aggregation in Cl.MC/C57.1 mast cells transfected with the control vector (pBK-CMV) or in Cl.MC/C57.1 cells transfected with the antisense expression vector (pBK-CMV-SYA-AS). Transfected mouse mast cells sensitized with anti-DNP IgE monoclonal antibody (mAb) for 2 hours were challenged with DNP-HSA. FIG. 7B illustrates IL-6 release from transfected Cl.MC/C57.1 mast cells 6 hours after stimulation by different concentrations of DNP-HSA. An asterisk indicates $P<0.05$ versus corresponding values for cells transfected with the control pBK-CMV vector (n=4 to 5 per point).

FIG. 8B). An asterisk indicates $P<0.01$ versus corresponding values for untransfected PC12 cells or PC12 cells that had been transfected with the control pBK-CMV vector (n=4 per point).

DETAILED DESCRIPTION OF THE INVENTION

Figure 1:
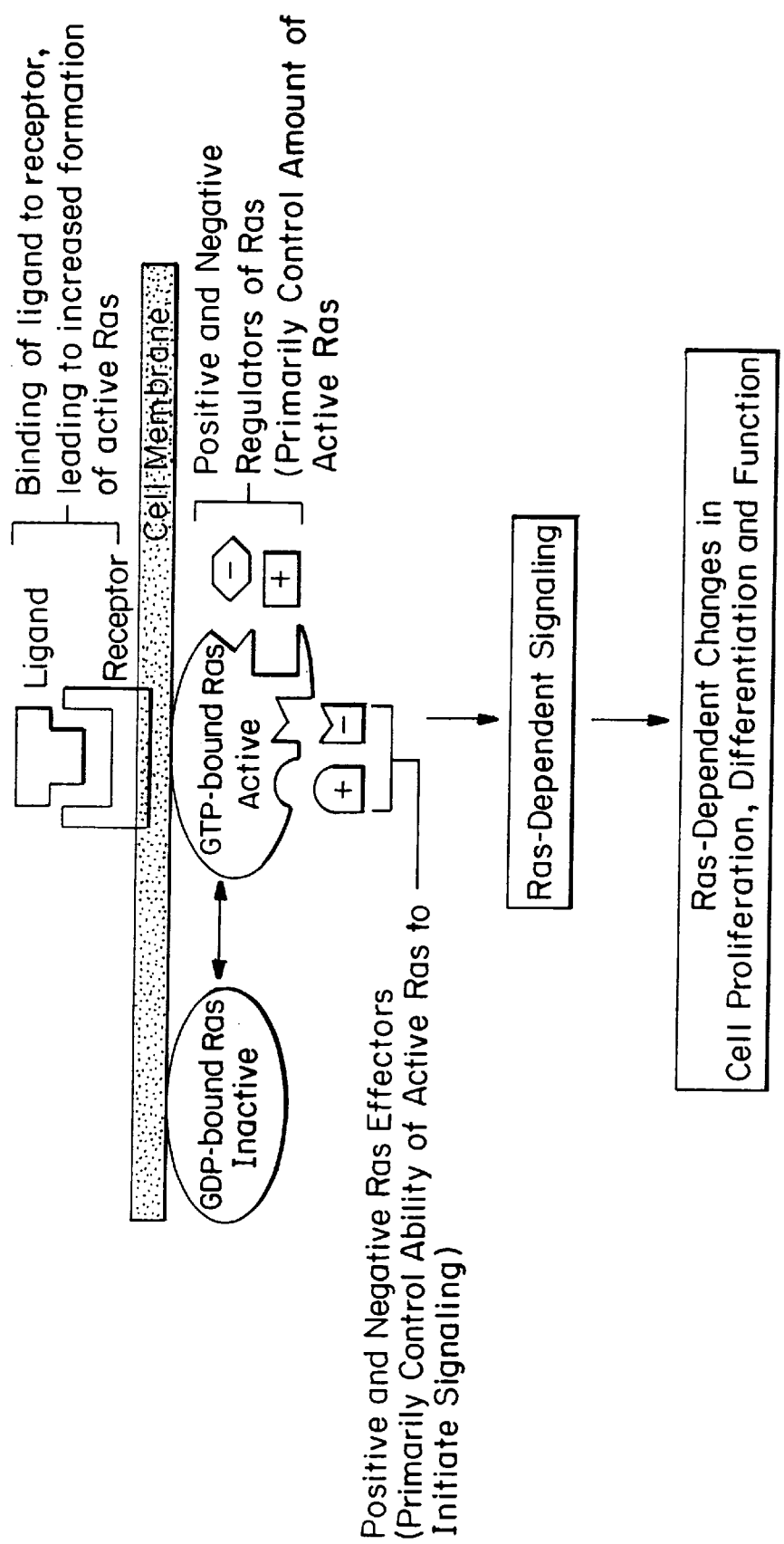
FIG. 1 is a schematic illustration of the pathways of Ras activation and Ras-dependent changes in cell proliferation, differentiation and function.
Figure 2:
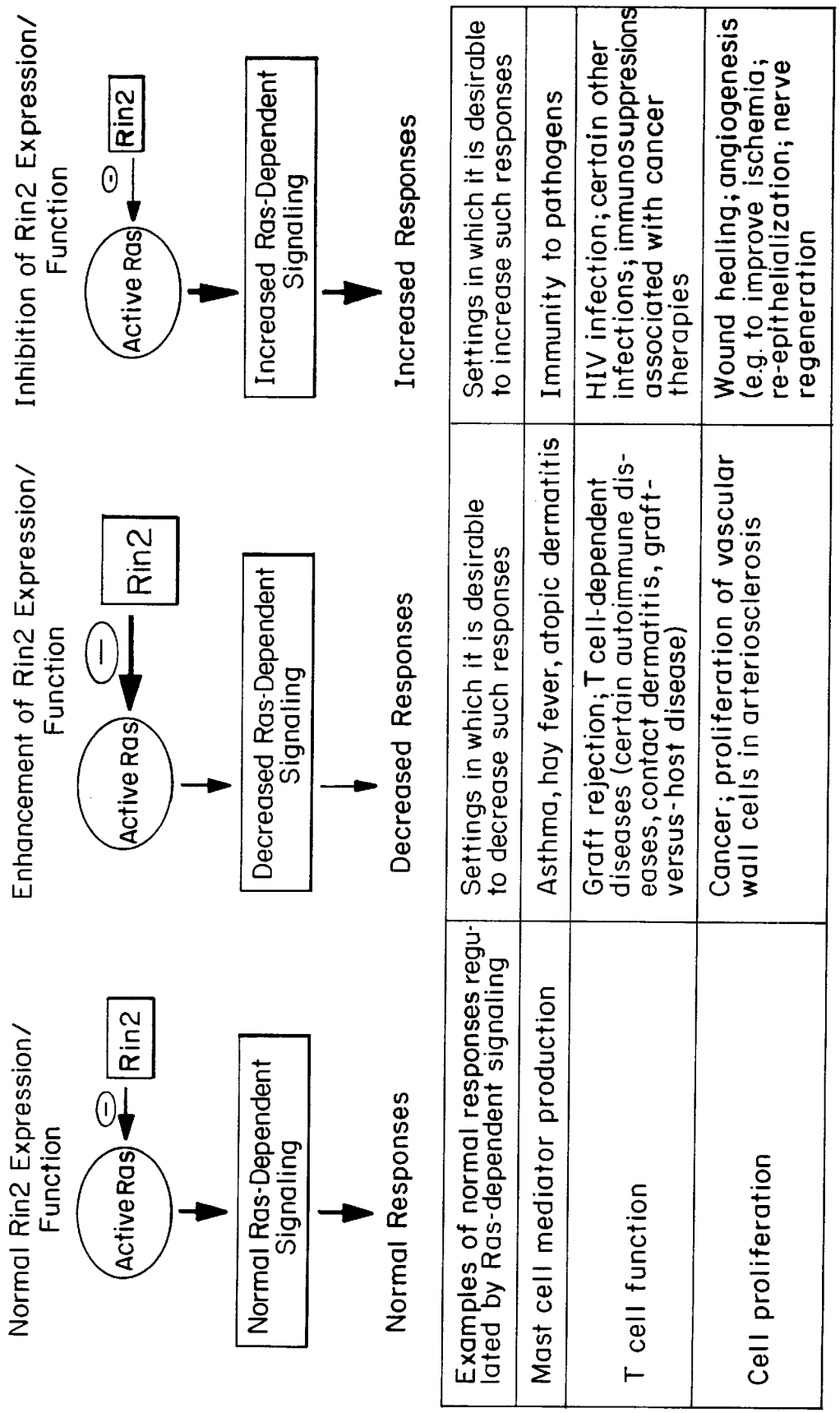
FIG. 2 is an illustration of alteration (increase or decrease) in Rin2 expression or activity and the corresponding effect on Ras-dependent signaling. Also illustrated are examples of instances in which it may be clinically desirable to alter Rin2 expression or activity and thereby alter, positively or negatively, Ras-dependent signaling.

In order to elucidate specific signaling pathways involved in FcεRI-mediated mast cell activation, the technique of mRNA differential display was used to isolate cDNAs of genes that were differentially expressed in mast cells stimulated through the FcεRI. Work described herein identified the cDNA of a novel gene, rin2, whose expression is rapidly increased in mammalian mast cells activated through FcεRI. The rin2 gene product shares significant homology with members of a class of Ras-binding proteins, such as Rin1 and JC265 (Colicelli et al., *Proc. Natl. Acad. Sci. USA*

88:2913–2917 (1991); Han and Colicelli, *Mol. Cell. Biol.* 15:1318–1323 (1995)), which have been shown to negatively regulate Ras-mediated signaling in *Saccharomyces* (*S.*) *cerevisiae*, and Vps9p (Burd et al., *Mol. Cell. Biol.* 16:2369–2377 (1996)), which is required for vacuolar protein sorting. As shown herein, inhibition of Rin2 expression potentiates both the intracellular signaling responses and the cellular secretory responses that are induced by FcεRI aggregation. The work described herein supports the role of Rin2 as a novel negative regulator/effector of Ras-dependent signaling pathways in mast cells.

The rin2 gene encodes a protein of predicted molecular mass of 56.9 kDa which shares significant homology to a class of Ras-binding proteins represented by JC265, Rin1 and Vps9p. Rin1 and JC265 were identified by virtue of their ability to suppress an activated Ras mutant allele in *S. cerevisiae*, indicating that they can negatively regulate Ras-induced signaling responses (Colicelli et al., *Proc. Natl. Acad. Sci. USA* 88:2913–2917 (1991)). In addition, recent studies have shown that Rin1 interacts directly with the Ras protein in a manner similar to that observed with Raf1 and yeast adenylyl cyclase, which are known downstream effectors of Ras (Han and Colicelli, *Mol. Cell. Biol.* 15:1318–1323 (1995)). Thus, Rin1 binds primarily to the effector domain of Ras and functions as a downstream effector of Ras-GTP. On the other hand, the gene encoding Vps9p was isolated in yeast by complementation of a vacuolar protein sorting defect associated with the vps9 mutant (Burd et al., *Mol. Cell. Biol.* 16:2369–2377 (1996)). Thus, Vps9p is a 53 kDa protein required for the proper sorting of several vacuolar proteins and may function as part of the vacuolar protein sorting machinery in *S. cerevisiae*.

The highest homology shared between JC265, Rin1, Vps9p, and Rin2 is found in the GTPase binding homology (GBH) domain regions in which three putative GBH motifs have been described (Burd et al., *Mol. Cell. Biol.* 16:2369–2377 (1996)). In particular, the GBH motif II is situated within the regions of JC265 and Rin1 that have been previously found to be shared with GAP and GAP-like proteins such as yeast IRA1 and IRA2, NF1, and sar1 (Colicelli et al., *Proc. Natl. Acad. Sci. USA* 88:2913–2917 (1991)). Furthermore, an FLP consensus motif can be detected within the GBH motif II regions of JC265, Rin1, Vps9p, and Rin2, and this FLP motif aligns well with the FLR consensus motif (residues 901–903) present in the block 3A region that is common to all GAP proteins (Scheffzek et al., *Nature* 384:591–596 (1996)). Mutation analysis has shown that the phenylalanine present at position 901 is required for core stabilization of the Ras protein and that leucine present at position 902 is important in the functional interaction between GAP and Ras (Miao et al., *J. Biol. Chem.* 271:15322–15329 (1996); Hettich and Marshall, *Cancer Res.* 54:5438–5444 (1994); Brownbridge et al., *J. Biol. Chem.* 268:10914–10919 (1993)). The presence of the FLP consensus motif in the Rin2 amino acid sequence provides additional support for the role of Rin2 as a regulator of Ras.

The invention pertains to an isolated nucleotide sequence encoding Rin2 protein. As appropriate, nucleic acid molecules of the present invention can be RNA, for example, mRNA, or DNA, such as cDNA and genomic DNA. DNA molecules can be double-stranded or single-stranded; single stranded RNA or DNA can be either the coding (sense) strand or the non-coding (antisense) strand. The nucleotide sequence can encode a portion of the amino acid sequence of the Rin2 protein; alternatively, the nucleotide sequence can include at least a portion of the Rin2 amino acid coding sequence along with additional non-coding sequences, such as introns and non-coding 3' and 5' sequences (including regulatory sequences, for example). Additionally, the nucleotide sequence can be fused to a marker sequence, for example, a sequence which encodes a polypeptide to assist in isolation or purification of the Rin2 protein. Such sequences include, but are not limited to, those which encode a glutathione-S-transfeRase (GST) fusion protein and those which encode a hemaglutin A (HA) peptide marker from influenza.

As used herein, "isolated" is intended to mean that the material in question exists in a physical milieu distinct from that in which it occurs in nature and/or has been completely or partially purified from other transcribed sequences (as in a cDNA or RNA library). Thus, an isolated gene or nucleotide sequence can include a gene or nucleotide sequence which is synthesized chemically or by recombinant means. Thus, recombinant DNA contained in a vector is included in the definition of "isolated" as used herein. Also, isolated nucleotide sequences include recombinant DNA molecules in heterologous host cells, as well as partially or substantially purified DNA molecules in solution. In vivo and in vitro RNA transcripts of the DNA molecules of the present invention are also encompassed by the term "isolated" nucleotide sequences. Such isolated nucleotide sequences are useful in the manufacture of the encoded protein, as probes for isolating homologous sequences (e.g., from other mammalian species), for gene mapping (e.g., by in situ hybridization with chromosomes), or for detecting expression of the rin2 gene in tissue (e.g., human tissue), such as by Northern blot analysis.

The present invention also pertains to nucleotide sequences which are not necessarily found in nature but which encode Rin2 protein. Thus, DNA molecules which comprise a sequence which is different from the naturally-occurring nucleotide sequence but which, due to the degeneracy of the genetic code, encode Rin2 protein are the subject of this invention. The invention also encompasses variations of the nucleotide sequences of the invention, such as those encoding portions, analogues or derivatives of Rin2 protein. Such variations can be naturally-occurring, such as in the case of allelic variation, or non-naturally-occurring, such as those induced by various mutagens and mutagenic processes. Included variations include, but are not limited to, addition, deletion and substitution of one or more nucleotides which can result in conservative or non-conservative amino acid changes, including additions and deletions. Preferably, the nucleotide or amino acid variations are silent or conserved, respectively; that is, they do not alter the characteristics or activity of Rin2 protein.

The invention described herein also relates to fragments of the isolated nucleic acid molecules described above. The term "fragment" is intended to encompass a portion of a nucleotide sequence described herein which is from at least about 25 contiguous nucleotides to at least about 50 contiguous nucleotides or longer in length; such fragments are useful as probes, e.g., for diagnostic methods and also as primers. Particularly preferred primers and probes selectively hybridize to the nucleic acid molecule encoding Rin2 protein described herein. For example, fragments which encode antigenic regions of the Rin2 protein described herein are useful.

The invention also pertains to nucleotide sequences which hybridize under medium stringency hybridization conditions (e.g., for selective hybridization) to a nucleotide sequence described herein. Appropriate stringency conditions which are considered "medium stringency" are known to those skilled in the art or can be found in standard texts such as *Current Protocols in Molecular Biology,* John Wiley & Sons, N.Y. (1989), 6.3.1–6.3.6. Preferred hybridization conditions allow for specific hybridization of a nucleotide sequence to a nucleotide sequence described herein. Such hybridizable nucleotide sequences are useful as probes and primers for diagnostic applications.

The invention pertains to nucleotide sequences which have a substantial identity with the nucleotide sequence of SEQ ID NO: 1; particularly preferred are nucleotide sequences which have at least about 90%, and more preferably at least about 95% identity with nucleotide sequences described herein. Particularly preferred in this instance are nucleotide sequences encoding polypeptides having at least one activity of the novel Rin2 protein described herein, or which hybridize with characteristic sequences of rin2 and can therefore be used as probes or primers. For example, preferred nucleotide sequences encoding a polypeptide having the same or similar biological activity as the Rin2 protein, and nucleotide sequences encoding a polypeptide with the same or similar immunogenic or antigenic properties as the Rin2 protein are within the scope of the invention. As used herein, activities of the Rin2 protein include, but are not limited to, catalytic activity, binding function, antigenic function and oligomerization function.

This invention also pertains to an isolated protein or polypeptide which is a novel Rin2 protein. Rin2 protein down-regulates the functional responses elicited by FceRI aggregation in mast cells, including down-regulating the amounts of preformed mediator (serotonin) and cytokine (IL-6) released from these cells upon FceRI-dependent stimulation. It may also down-regulate responses elicited at other types of receptors (such as TrkA receptors for NGF, c-kit receptors for SCF, etc.) in response to receptor interaction with ligand or due to auto-activation of the receptors (e.g., by activating mutations).

For example, an isolated protein of the invention may be substantially isolated with respect to the complex cellular milieu in which it naturally occurs. In some instances, the isolated material will form part of a composition (for example, a crude extract containing other substances), buffer system or reagent mix. In other circumstances, the material may be purified to essential homogeneity, for example as determined by PAGE or column chromatography such as HPLC. According to the invention, the amino acid sequence of the polypeptide can be that of the naturally-occurring protein or can comprise alterations therein. Such alterations include conservative or non-conservative amino acid substitutions, additions and deletions of one or more amino acids; however, such alterations should preserve at least one activity of the Rin2 protein, i.e., the altered or mutant protein should be an active derivative of the naturally-occurring protein. For example, the mutation(s) can preferably preserve the three dimensional configuration of the binding and/or catalytic site of the native protein. The presence or absence of Rin2 activity can be determined by various functional assays, as described herein. Moreover, amino acids which are essential for the function of the Rin2 protein can be identified by methods known in the art. Particularly useful methods include identification of conserved amino acids in the family or subfamily of Ras-interference or Ras-inhibiting proteins, site-directed mutagenesis and alanine-scanning mutagenesis (for example, Cunningham and Wells, *Science* 244:1081–1085 (1989)), crystallization and nuclear magnetic resonance. The altered polypeptides produced by these methods can be tested for particular biologic activities, including immunogenicity and antigenicity.

Specifically, appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan (see, for example, FIG. 4); further appropriate amino acid changes can also be found in Bowie et al. (*Science* 247:1306–1310(1990)).

The Rin2 polypeptide can also be a fusion protein comprising all or a portion of the Rin2 amino acid sequence fused to an additional component. Additional components, such as radioisotopes and antigenic tags, can be selected to assist in the isolation or purification of the polypeptide or to extend the half life of the polypeptide; for example, a hexahistidine tag permits ready purification by nickel chromatography.

Also included in the invention are novel polypeptides which are at least about 40% similar to the Rin2 protein described herein. However, polypeptides exhibiting lower levels of identity are also useful, particularly if they exhibit high, e.g., at least about 40%, similarity over one or more particular domains of the protein. For example, polypeptides sharing high degrees of identity or similarity over domains necessary for particular activities, including binding and enzymatic activity, are included herein. As used herein, "similar" amino acids are intended to mean identical amino acids or conserved substitutions of amino acids.

Polypeptides described herein can be isolated from naturally-occurring sources, chemically synthesized or recombinantly produced. Polypeptides or proteins of the present invention can be used as a molecular weight marker on SDS-PAGE gels or on molecular sieve gel filtration columns using art-recognized methods.

The invention also provides expression vectors containing a nucleic acid sequence encoding a polypeptide which is a Rin2 polypeptide, operably linked to at least one regulatory sequence. Many such vectors are commercially available, and other suitable vectors can be readily prepared by the skilled artisan. "Operably linked" is intended to meant that the nucleotide sequence is linked to a regulatory sequence in a manner which allows expression of the nucleic acid sequence in a host cell. Regulatory sequences are art-recognized and are selected to produce a polypeptide which is Rin2. Accordingly, the term "regulatory sequence" includes promoters, enhancers, and other expression control elements which are described in Goeddel, *Gene Expression Technology: Methods in Enzymology* 185, Academic Press, San Diego, Calif. (1990). For example, the native regulatory sequences or regulatory sequences native to a transformed host cell can be employed. It should be understood that the design of the expression vector may depend on such factors as the choice of the host cell to be transformed and/or the type of protein desired to be expressed. For instance, the polypeptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression,* ed. M. Inouye (Academic Press, 1983) p. 83; *Molecular Cloning: A Laboratory Manual,* 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to geneticin, neomycin, tetracycline, ampicillin, chloramphenicol, kanamycin and streptomycin resistance.

Prokaryotic and eukaryotic host cells transfected by the described vectors are also provided by this invention. For instance, cells which can be transfected with the vectors of the present invention include, but are not limited to, bacterial cells such as E. coli (e.g., E. coli K12 strains), Streptomyces, Pseudomonas, Serratia marcescens and Salmonella typhimurium, insect cells (baculovirus), including Drosophila, fungal cells, such as yeast cells, plant cells and mammalian cells, such as mast cells, PC12 cells, EL-4 T cells or other T cells, Chinese hamster ovary cells (CHO) and COS cells.

Thus, a nucleotide sequence derived from the cloning of Rin2 described herein can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect, plant or mammalian) or prokaryotic (bacterial cells), are standard procedures used in producing other well known proteins. Similar procedures, or modifications thereof, can be employed to prepare recombinant proteins according to the present invention by microbial means or tissue-culture technology. Accordingly, the invention pertains to the production of Rin2 proteins or polypeptides by recombinant technology.

The proteins and polypeptides of the present invention can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

The present invention also relates to antibodies which bind a polypeptide which is Rin2. For instance, polyclonal and monoclonal antibodies, including non-human and human antibodies, humanized antibodies, chimeric antibodies and antigen-binding fragments thereof (Current Protocols in Immunology, John Wiley & Sons, N.Y. (1994); EP Application 173,494 (Morrison); International Patent Application WO86/01533 (Neuberger); and U.S. Pat. No. 5,225, 539 (Winters)) which bind to the described protein are within the scope of the invention. A mammal, such as a mouse, rat, hamster or rabbit, can be immunized with an immunogenic form of Rin2 (e.g., Rin2 or a peptide comprising an antigenic fragment of Rin2 which is capable of eliciting an antibody response). Techniques for conferring immunogenicity on a protein or peptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the art (Kohler and Milstein, Nature 256:495–497 (1975); Kozbar et al., Immunology Today 4:72 (1983); and Cole et al., Monoclonal Antibodies and Cancer Therapy, Alan R. Liss, Inc., pp. 77–96 (1985)). The term "antibody" as used herein is intended to include fragments thereof, such as Fab and F(ab)$_2$. Antibodies described herein can be used to inhibit the activity of Rin2 described herein, particularly in vitro and in cell extracts, using methods known in the art. Additionally, such antibodies, in conjunction with a label, such as a radioactive label, can be used to assay for the presence of the expressed protein in a cell from, e.g., a tissue sample, and can be used in an immunoabsorption process, such as an ELISA, to isolate the Rin2 protein. Tissue samples which can be assayed include human tissues, e.g., differentiated and non-differentiated cells. Examples include, but are not limited to, heart, lung, skin, bone marrow, thymus, lymph node, kidney, liver, brain, pancreas, gastrointestinal tract, gonads (testes, ovaries), fibroblasts and epithelium.

The present invention also pertains to pharmaceutical compositions comprising polypeptides described herein. For instance, a polypeptide or protein, or prodrug thereof, of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to well known procedures, and will depend on the ultimate pharmaceutical formulation desired. Methods of introduction of exogenous peptides at the site of treatment include, but are not limited to, intradermal, intramuscular, intraperitoneal, intravenous, subcutaneous, oral, intranasal intrarectal, intravaginal, and aerosol (for administration to the respiratory tract). Other suitable methods of introduction can also include gene therapy, rechargeable or biodegradable devices and slow release polymeric devices. The pharmaceutical compositions of this invention can also be administered as part of a combinatorial therapy with other agents.

While the intracellular events which lead to the activation of cell proliferation, differentiation, or functional responses (e.g., FcεRI-dependent mast cell mediator secretion) have been investigated in great detail, equally as interesting are the pathways which can suppress such responses. For example, recent evidence indicates that certain cell surface receptors, such as FcγRIIb or gp149 in mast cells, can mediate signals which can down-regulate the cell activation signals which are transduced by other cell surface receptors, including the mast cell FcεRI (Scharenberg and Kinet, Cell 87:961–964 (1996)). However, the work described herein is directed to searching for intracellular molecules which function to down-regulate the signaling pathways in which Ras plays a role, including those which govern the secretion of mast cell mediators or the proliferative responses of neuronal cells or other cell types. Ras plays a pivotal role in signaling pathways which mediate diverse cellular responses to a spectrum of receptor-ligand interactions (Bourne et al., Nature 348:125–132 (1990); Marshall, FASEB J. 9:1311–1318 (1995)). Recent studies have shown that the functional activation of mast cells which is induced by the aggregation of FcεRI by IgE and specific antigen is associated with the activation of Ras and its effector pathways (Beaven and Baumgartner, Curr. Opin. Immunol. 8:766–772 (1996); Jabril-Cuenod et al., J. Biol. Chem. 271:16268–16272 (1996)).

FcεRI-mediated Ras activation in mast cells is accompanied by activation of the Shc-Grb2-Sos pathway, which precedes Ras activation, as well as the Ras effector pathway of Raf-1/Erk-MAP kinases (Jabril-Cuenod et al., J. Biol. Chem. 271:16268–16272 (1996)). Recent studies with rat RBL-2H3 mast cells have demonstrated that FcεRI-induced Ras activation results in a transcription activation mediated by Elk-1 and NFAT (Turner and Cantrell, *J. Exp. Med.* 185:43–53 (1997)). The Elk-1 transcription factor exerts its effects by interacting with the serum response element, which is a regulatory component of early response genes such as c-fos (Treisman, *Curr. Opin. Genet. Dev.* 4:96–101 (1994)), whereas members of the NFAT transcription factor family form regulatory complexes with inducible nuclear factor such as Fos or Jun (Rao, *Immunol. Today* 15:274–281 (1994)). Such complexes interact with cytokine gene promoters and activate transcriptions of genes for IL-2, IL-4, GM-CSF, and TNF-α (Rao, *Immunol. Today* 15:274–281 (1994)). In mast cells, NFAT is implicated in the regulation of transcription of the IL-4 gene (Weiss et al., *Mol. Cell. Biol.* 16:228–235 (1996)). Interestingly, the activation of the Raf-1/MEK/Erk cascade is necessary and sufficient for the activation of Elk-1 in mast cells, whereas the induction of NFAT by FcεRI stimulation requires the activity of Rac-1 (Turner and Cantrell, *J. Exp. Med.* 185:43–53 (1997)). Earlier studies have shown that Rin1 interacts directly with Ras in a manner that is characteristic of Raf-1, suggesting that Rin1 is a negative downstream effector of Ras (Han and Colicelli, *Mol. Cell. Biol.* 15:1318–1323 (1995)).

As shown herein, reduced expression of Rin2 can dramatically potentiate the downstream signaling responses mediated by Ras. In mouse mast cells transfected with the rin2 antisense expression vector, the induction of early-response gene expression and the activation of MAP kinase activity in response to FcεRI crosslinking are significantly augmented, as compared with those observed in mast cells transfected with a control vector. These results support a role of Rin2 as a negative effector/regulator of Ras. Furthermore, reduced expression of Rin2 can markedly enhance the functional responses elicited by FcεRI aggregation in mouse mast cells; the expression of antisense rin2 in mouse mast cells can significantly increase the amounts of preformed mediators (e.g., 5-HT) and cytokine (e.g., IL-6) released from these cells upon FcεRI-dependent stimulation. These data indicate that Rin2 can negatively regulate the Ras-mediated signaling responses in mast cells that lead to both the release of preformed mediators and the transcription of cytokine genes and the secretion of the corresponding products. Stimulation of mast cells by IgE and antigen results in Ras activation followed by a rapid and transient induction of rin2 mRNA expression. Rin2 appears to exert its effects by down-regulating the signaling and functional responses elicited by FcεRI aggregation. Thus, during the period subsequent to mast cell activation, Rin2 may function as a cellular switch in turning off ongoing signaling initiated by Ras activation. In mast cells, such a regulatory process may be important as a feedback mechanism to restore the perturbed cellular environment to its normal basal physiological state after the cessation of cell activation.

Furthermore, rin2 mRNA expression is significantly elevated in mouse mast cells stimulated with stem cell factor (SCF), with a kinetics of activation that is very similar to that which is observed in mast cells after FcεRI-dependent stimulation. SCF, the cognate ligand for the c-kit tyrosine kinase receptor, is a major mast cell growth factor which has been shown to be critical in the maturation and development/function of rodent and human mast cells (Galli et al., *Adv. Immunol.* 55:1–96 (1994)). The interaction of SCF with the c-kit tyrosine kinase receptor has been shown to induce an activation of Ras and its effector pathways via the activation of the Shc-Grb2-Sos signaling pathway (Duronio et al., *Proc. Natl. Acad. Sci. USA* 89:1587–1591 (1992); Tauchi et al., *J. Exp. Med.* 179:167–175 (1994)).

As shown herein, nerve growth factor (NGF) can also elicit a rapid and sustained induction of expression of rin2 mRNA transcript through it receptor. NGF has been shown to induce neuronal differentiation and cessation of cell proliferation in PC12 cells via its interaction with TrkA receptor tyrosine kinase (Barbacid, *J. Neurobiol.* 25:1386–1403 (1994); Bothwell, *Ann. Rev. Neurosci.* 18:223–253 (1995)). PC12 cells are a commonly used in vitro model of neuronal development and function (Greene and Tischler, *Proc. Natl. Acad. Sci. USA* 73:2424–2428 (1976)). Previous studies have indicated that NGF stimulation of TrkA receptors in PC12 cells leads to Ras activation and the activation of the Raf-1/MEK/MAP kinases effector pathway (Thomas et al., *Cell* 68:1031–1040 (1992); Wood et al., *Cell* 68:1041–50 (1992)). Results presented herein show that PC12 cells which have been transfected with the pBK-CMV-SYA-AS vector and therefore have reduced expression of Rin2 can still differentiate in response to NGF stimulation. However, these transfected cells exhibit a higher rate of cell proliferation than that detected in control PC12 cells. This effect is observed in both unstimulated transfected PC12 cells and transfected PC12 cells stimulated with NGF. NGF is also known to have a transient proliferative effect on PC12 cells, which precedes the better known anti-mitogenic effects of NGF on these cells. Thus, by suppressing Ras-dependent proliferative effects, Rin2 may play a role in mediating the anti-mitogenic effects of NGF on these neuronal cells. Taken together, these data indicate that the expression of the rin2 gene transcript can be differentially regulated in mast cells and in PC12 cells via different ligand-receptor interactions.

As disclosed herein, activation of a mouse T cell lymphoma line (EL-4 cells) via the T cell receptor, by stimulating the cells with antibodies directed against CD3 and CD28, also elicits a rapid and transient induction of expression of rin2 mRNA transcript. T cells are essential for the expression of an adequate immune response, but inappropriate activation of T cells is thought to contribute to a wide variety of diseases with "autoimmune" components, such as autoimmune (Type I) diabetes mellitus, rheumatoid arthritis, ankylosing spondylitis, sarcoidosis, Sjögren's syndrome, multiple sclerosis, inflammatory bowel disease (i.e., Crohn's disease and ulcerative colitis), dermatomyositis, scleroderma, polymyositis, systemic lupus erythematosus, biliary cirrhosis, autoimmune thyroiditis, and autoimmune hepatitis, as well as many dermatological disorders, including psoriasis, contact sensitivity and atopic dermatitis (Schwartz, Autoimmunity and Autoimmune Diseases, in *Fundamental Immunology*, Third Edition, Paul, ed. (Raven Press, N.Y., pp. 1033–1097 (1993)); Rich, *Clinical Immunology*: Principles and Practice, Mosby, St. Louis (1996)). T cells are also important in the process of tissue graft rejection, such as grafts of bone marrow, hematopoietic stem cells, skin, heart, lung, liver, kidney, pancrease and isntestine, among others, and in graft-versus-host disease; T cells can also undergo neoplastic transformation, resulting in the development of leukemias or lymphomas. The findings with EL-4 T cells disclosed herein support the role of Rin2 as a negative Ras effector/regulator mediating diverse cellular responses in T cells. Taken together with the results disclosed herein regarding the role of Rin2 in regulating cellular responses in mast cells and PC12 adrenal pheochromocytoma cells, the findings in EL-4 T cells are also consistent with the hypothesis that Rin2 is a negative Ras effector/regulator mediating diverse functional responses in different cell types. There are likely to be many other cell types in which Rin2 may down-regulate Ras-dependent functional responses, since Ras is involved in influencing functional responses in diverse cell types (Marshall, *FASEB*

J 9:1311–1318 (1995)). Additionally, cells which express the FcεRI receptor, T cell receptor, TrkA and c-kit, as well as diverse other receptors which signal by mechanisms which are influenced by Ras, can have their Ras-dependent functional responses negatively regulated by Rin2.

It will be apparent to the skilled artisan that the identification of the novel protein Rin2, which can inhibit Ras-dependent cellular signaling, has many commercial applications. The Ras effector signaling pathways have been shown to be important in mediating signal transduction from the cell membrane to the nucleus in many oncogenic, mitogenic, and developmental processes.

As a result of Rin2's ability to inhibit IgE and antigen-dependent release of mediators from mast cells, compositions which can enhance Rin2 expression and/or function, or which mimic these actions (e.g., molecules synthesized based on the structure/functional characteristics of the Rin2 protein), can be used to inhibit mediator release from effector cells in disorders such as asthma and other allergic diseases (e.g., hay fever and atopic eczema), thus ameliorating these disorders.

The ability of Rin2 to negatively regulate Ras-dependent signal transduction in other cell types (in addition to mast cells) suggests that compounds (e.g., isolated Rin2, Rin2 "mimics" or agents that can enhance expression of native Rin2) that are able to block such Ras-dependent cellular signaling pathways can produce clinically desirable effects. Mutated forms of cellular Ras genes, resulting in oncogenic activation of Ras proteins, have been found to be among the most common genetic abnormalities associated with human cancer. The early stage in multistage tumor progression has been associated with Ras activation, and disruption of the oncogenic Ras genes in colon cancer cell lines has been shown to revert the cells to a more regulated state of growth (Shirasawa et al., *Science* 260:85–88). Thus, the rin2 cDNA clone can be used to identify compounds that can block Ras-induced cell transformation in vitro. These compounds can include isolated Rin2 (e.g., overexpression of Rin2), derivatives (modified forms) of Rin2, and compounds identified by another method, e.g., computer modeling of compounds designed with reference to structures and/or characteristics of Rin2 and synthesized by known methods (e.g., chemical synthesis, peptide chemistry). These compounds can be tested for their ability to function as Ras-specific anti-neoplastic agents for the treatment of cancer, or as Ras-specific agents which inhibit other examples of clinically unwanted, but non-neoplastic, Ras-dependent cellular proliferation.

Mutations in the genes encoding other molecules which are involved in Ras-dependent intracellular signaling have been linked to human diseases with a genetic component, such as some cases of melanoma. The rin2 cDNA clone can be used to map, identify and isolate or clone the human counterpart of the rin2 gene and, ultimately, to assess whether mutations of Rin2 and/or genes identified using Rin2 are linked to known human diseases.

The rin2 cDNA clone can be used in a yeast two-hybrid system to identify other novel cellular proteins that interact with Rin2 and/or Ras and thus regulate the signaling responses along Ras effector pathways. Using a yeast two-hybrid system (Fields and Sternglanz, *Trends Genet.* 10:286–292 (1994)), specific regions of the Rin2 protein that interact with Ras can be identified. The elucidation of the mechanism of protein-protein interaction between Rin2 and Ras will be useful in the development of small molecule drugs that interact specifically with Ras and inhibit or enhance its function.

Using the rin2 cDNA clone, the Rin2 protein can be produced using a protein expression system. The partially purified Rin2 protein, or a synthetic peptide based on the known Rin2 amino acid sequence, can be used to raise Rin2-specific antibodies which can be utilized as laboratory reagents for studying the Ras effector pathways, as well as "humanized" antibodies for potential clinical applications. Rin2 is an intracellular protein. Thus, small fragments of antibodies against Rin2, perhaps specifically modified to enhance their ability to identify specific cell types and to pass through the cells' surface (plasma membrane), may be required to gain appropriate access to the intracellular Rin2 target.

However, other natural or newly-synthesized chemicals that, because of their properties, can readily enter cells and achieve intracellular concentrations which are sufficient to permit the expansion of the desired interactions with Rin2, can be identified via their ability to interact with Rin2, Rin2 fragments or Rin2-mimicking compounds, in various in vitro systems. Rin2-mimicking compounds are defined herein as peptide or protein compounds which may be unrelated to Rin2 in amino acid sequence, or non-peptide based compounds, which express sufficient structural similarity to native Rin2 or fragments thereof to permit such compounds to be used for initial screening of compounds, including those generated through recombinatorial chemistry approaches, to identify those which can interact with active Rin2 sufficiently to enhance or inhibit its function.

As used herein, "inhibition" is intended to encompass any reduction in the quality or quantity of the assessed activity, including complete abolishment thereof. The term "enhancement" as used herein is intended to mean any increase in the quality or quantity of the assessed activity, including increases resulting from mimicking of an assessed activity. As used herein, "alteration"" is intended to mean either inhibition or enhancement of the quality or quantity of the assessed activity. As used herein, "mimicking" is intended to mean that the assessed activity is substantially similar to the corresponding activity of Rin2.

Depending on the circumstances, it may be desirable either to inhibit or to enhance Rin2 activity, in order to enhance or to suppress, respectively important Ras-dependent signaling pathways. Several examples of the inhibition of Rin2 activity, resulting in reduced Rin2-dependent inhibition of Ras-dependent pathways, with subsequent enhancement of such pathways, can be envisioned. Enhancement of Ras-dependent pathways promoting the proliferation and functional activation of cells involved in wound healing, including the development of new blood vessels (i.e., angiogenesis) in areas of ischemic tissue (e.g., in tissues such as cardiac or skeletal muscle, which are ischemic because of the consequences of arteriosclerosis), can have great therapeutic benefit. Enhancement of the Ras-dependent pathways which contribute to the proliferation of, and production of mediators and cytokines by, T cells and mast cells, and other cell types activated through the same or distinct receptors, may be of great benefit in diseases that are associated with diminished numbers and/or function of these cells, such as in patients infected with the human immunodeficiency virus (HIV), or receiving treatment with radiation or chemical agents for the treatment of cancer. Enhancement of Ras-dependent signaling in neuronal cells in response to NGF or other neurotrophic factors may be desirable in settings characterized by neuronal loss, or when neural regeneration is an objective (Satoh et al., *Mol. Cell. Biol.* 7:4553–4556 (1987); Szeber'nyi et al., *Mol. Cell. Biol.* 10:5324–5332 (1990); Qiu and Green, *Neuron*

7:937–946 (1991); Muroya et al., *Oncogene* 7:277–281 (1992)). For example, Ras-dependent pathways, such as the functional responses elicited by FcεRI aggregation, can be inhibited by enhancing the activity of Rin2. Agents which enhance Rin2 activity include, but are not limited to, isolated Rin2, Rin2 mimics or agents that can enhance expression of native Rin2.

In contrast, enhancement of Rin2 activity, resulting in increased Rin2-dependent inhibition of Ras-dependent pathways, with subsequent inhibition of such pathways, can also be useful. For example, it may be desirable to inhibit TCR- and Ras-dependent pathways promoting the proliferation and functional activation of cells involved in tissue graft rejection, graft-versus-host disease, and autoimmune disorders or T cell-associated disorders, e.g., autoimmune (Type I) diabetes mellitus, rheumatoid arthritis, ankylosing spondylitis, sarcoidosis, Sjögren's syndrome, multiple sclerosis, inflammatory bowel disease (i.e., Crohn's disease and ulcerative colitis), dermatomyositis, scleroderma, polymyositis, systemic lupus erythematosus, biliary cirrhosis, autoimmune thyroiditis, and autoimmune hepatitis, as well as many dermatological disorders, including psoriasis, contact sensitivity and atopic dermatitis. In asthma and allergic diseases such as hay fever and atopic dermatitis, it is desirable to inhibit the Ras-dependent functional responses induced by FcεRI aggregation in cells bearing the FcεRI receptor, e.g., mast cells. Specifically, the intracellular signaling (e.g., activation of MAP kinase) and cellular secretory responses (e.g., release of preformed mediators, such as 5-HT, and cytokines, such as IL-6) can be inhibited by enhancing Rin2 activity. Additionally, enhancement of Rin2 activity can also be used to inhibit cellular proliferation through the TrkA receptor, e.g., in PC12 cells, and to inhibit Ras-dependent cellular proliferation, including cancers or other unwanted neoplastic or non-neoplastic proliferation of cells.

Alteration of Rin2 activity can be accomplished by increasing or decreasing the amount of Rin2 protein present to inhibit or enhance, respectively, Ras-dependent pathways, the activity of the Rin2 protein, or both. For example, the activity of the Rin2 protein described herein can be enhanced by overexpressing isolated Rin2 protein from an appropriate expression construct in a host cell. Alternatively, a cell population of interest can be treated with one or more agents, such as SCF, that enhance expression or activity of native Rin2 present in the cell population. Additionally, compounds which mimic Rin2 activity are useful in applications in which native or isolated Rin2 are useful. Useful compounds will be able to mimic at least one appropriate activity of Rin2, e.g., binding activity, catalytic activity, and include fragments and derivatives of Rin2. Alternatively, Ras-dependent pathways can be enhanced by inhibiting the activity of Rin2. Agents which inhibit Rin2 activity include, but are not limited to, agents that can inhibit expression of native Rin2 and agents which bind native Rin2.

The invention also pertains to methods of inhibiting functional responses induced by Ras-dependent signaling pathways in a mammal by administering to the mammal an effective amount of an agent which enhances the activity of Rin2. The invention also pertains to methods of inhibiting cellular proliferation in a mammal by administering to the mammal an effective amount of an agent which enhances the activity of Rin2. The invention also encompasses methods of inhibiting Ras-dependent cellular proliferation, including cancers, neoplastic and non-neoplastic proliferation, in a mammal by administering to the mammal an effective amount of an agent which enhances the activity of Rin2.

The invention also pertains to methods of enhancing functional responses induced by Ras-dependent signaling pathways in a mammal by administering to the mammal an effective amount of an agent which inhibits the activity of Rin2.

The present invention also relates to an assay for identifying agents which alter the activity of Rin2, such as agents which enhance or inhibit the activity of Rin2. For example, a cell containing the Rin2 protein, or an active fragment or derivative thereof, can be activated via a specific receptor that induces signaling that is modulated by Rin2, in the presence of an agent to be tested, and the level of Rin2 activity can be assessed; in a preferred embodiment, the level of Rin2 activity can be assessed and compared with the corresponding level in a control in the absence of the agent to be tested. The activity of Rin2 protein can be assessed directly, e.g., by assessing the expression levels of the protein, or indirectly, such as by assessing functional responses e.g., activation of MAP kinase activity or secretion of 5-HT or IL-6. The cell containing Rin2, or a derivative or portion thereof having Rin2 activity, can be contacted directly or indirectly with the stimulus in the presence of the agent to be tested. Enhancement of Rin2 activity, or an increase in the level of Rin2 activity relative to a control, indicates that the agent is an agonist of Rin2 activity. Similarly, inhibition of Rin2 activity, or a decrease in the level of Rin2 activity relative to a control, indicates that the agent is an antagonist of Rin2 activity.

The present invention also relates to novel agents identified by the assay described above. Agents identified by the assay described herein may enhance (e.g., prolong or increase) or inhibit (e.g., shorten or decrease) the activity of the Rin2 protein.

The following Examples are offered for the purpose of illustrating the present invention and are not to be construed to limit the scope of this invention. The teachings of all references cited herein are hereby incorporated herein by reference.

EXAMPLES

Materials and Methods

Cytokines, cDNA Probes and Antibodies

Recombinant mouse IL-3 was purchased from BioSource International (Camarillo, Calif.). The c-fos probe is a 1.2 kb HindIII/EcoRI mouse cDNA fragment generously provided by Dr. Brent Cochran. The cDNA probes were labeled with [α-$^{32}$P] dCTP (6000 mCi/mmol) (New England Nuclear, Boston, Mass.) using the exo(−) Klenow fragment of DNA polymeRase I with random nonamer primers (Stratagene, La Jolla, Calif.). Purified mouse 2.5 S NGF was purchased from Upstate Biotechnology (Lake Placid, N.Y.). For T-cell activation experiments, purified hamster anti-mouse CD3ε and anti-mouse CD28 monoclonal antibodies were purchased from Pharmingen (San Diego, Calif.).

Cell Culture

Bone marrow-derived cultured mast cells (BMCMCs) were obtained by maintaining the femoral bone marrow cells of 4–6 week-old BALB/c mice in suspension in IL-3-containing conditioned medium, consisting of 10% heat-inactivated fetal calf serum (FCS) (Sigma Chemical Company, St. Louis, Mo.), $5 \times 10^{-5}$ M 2-mercaptoethanol (Sigma) and 2 mM L-glutamine (GIBCO Laboratories, Grand Island, N.Y.) in Dulbecco's Modified Eagle's Medium (DMEM; GIBCO Laboratories, Grand Island, N.Y.) (complete medium) supplemented with 20% (v/v) of either supernatants from Concanavalin A-activated spleen cells or WEHI-3 cell-conditioned medium (Nabel et al., Nature 291:332–334 (1981); Galli et al., *J. Cell Biol.* 95:435–444 (1982)). The cells were resuspended in fresh conditioned medium 1–2 times a week. After 4–5 weeks, at least 95% of cells that remained in the cultures were identifiable as mast cells, as determined by neutral red or May-Grünwald/Giemsa staining. Cl.MC/C57.1 cells, a cloned growth factor-independent mouse mast cell line of BALB/c origin (Young et al., *Proc. Natl. Acad. Sci. USA* 84:9175–9179 (1987); Tsai et al., *FASEB J.* 10, Abstract A1268 (1996)), were maintained in complete medium lacking exogenous growth factors. PC12 cells, a rat adrenal pheochromocytoma cell line, were obtained from American Type Culture Collection (ATCC No. CRL1721). They were grown in RPMI 1640 medium supplemented with 10% horse serum (HS) and 5% FCS. EL-4 cells, a mouse lymphoma T cell line, were obtained from ATCC (ATCC No. TIB39) and grown in DMEM medium supplemented with 10% HS.

FcεRI Cross-Linking

The IgE anti-DNP mAb-producing hybridoma H1-DNP-ε-26 (Liu et al., *J. Immunol.* 124:2728–2737 (1980)), generously provided by Drs. F.-T. Liu and D. H. Katz, was used to generate ascites. BMCMC or Cl.MC/C57.1 mast cells were sensitized with the ascites diluted 500-fold in complete medium (final IgE concentration of approximately 8 $\mu$g/ml) for 2 hours at 37° C., washed with medium, then resuspended with medium containing $DNP_{30-40}$-HSA (Sigma) at 50 ng/ml at 37° C. These conditions of sensitization with IgE and stimulation with specific antigen have been shown to be adequate for the activation of such cells for [$^3$H]5-HT release (Gordon and Galli, *J. Exp. Med.* 174:103–107 (1991)).

mRNA Differential Display

Differential display was performed using the RNAmap KitA (GenHunter, Nashville, Tenn.) according to the manufacturer's specifications. Specifically, total RNA was extracted from cultured cells using the RNAzol B method (Biotecx Laboratories, Houston, Tex.) and subsequently digested with DNaseI (1 unit/10 $\mu$g) (Promega, Madison, Wis.) for 30 minutes at 37° C. Approximately 2 $\mu$g of digested RNA was subjected to the reverse transcription reaction with one of the four $T_{12}MN$ anchored primers (N=G, A, T, or C) at 65° C. for 5 minutes, at 37° C. for 60 minutes, and then at 95° C. for 5 minutes. The MMLV reverse transcriptase (100 units) was added after 10 minutes of incubation at 37° C. The resulting cDNAs were further amplified by PCR (final volume, 20 $\mu$l) with GeneAmp 1×PCR Buffer (Perkin Elmer, Foster City, Calif.), 2 $\mu$MdNTPs, 0.2 $\mu$M AP-primers (AP-1: 5'-AGCCAGCGAA-3' (SEQ ID NO: 3); AP-2: 5'-GACCGCTTGT-3' (SEQ ID NO: 4); AP-3: 5'-AGGTGACCGT-3' (SEQ ID NO: 5); AP-4: 5'-GGTACTCCAC-3' (SEQ ID NO: 6); and AP-5: 5'-GTTGCGATCC-3' (SEQ ID NO: 7)), 1 $\mu$M $T_{12}MN$ primer (the same primer used in the respective reverse transcription reaction), 2 $\mu$l reverse transcription mix, 1 $\mu$l $^{35}$S-dATP (1200 Ci/mmol) (NEN, Boston, Mass.), and 1 unit AmpliTaq DNA polymeRase (Perkin Elmer) at 94° C. for 30 seconds, 40° C. for 2 minutes, and 72° C. for 30 seconds for 40 cycles, followed by an additional 5 minutes at 72° C. 3.5 $\mu$l of each sample was run on 6% sequencing gels. Differentially-expressed PCR products were excised from the gel, extracted with water, and reamplified by PCR using the same set of primers. The reamplified PCR segments were $^{32}$P-labeled as probes for Northern blot analysis, or subcloned into pGEM-T Vector (Promega) and sequenced using Sequenase version 2.0 (U.S. Biochemical, Cleveland, Ohio).

Northern Hybridization

Total RNA was prepared from cultured cells or from mouse tissues using the RNAzol B method (Biotecx) according to the manufacturer's specifications; 10 or 15 $\mu$g of total RNA were loaded in each lane and electrophoresed in 1% agarose-formaldehyde denaturing gel, and then transferred onto Zetabind nylon membrane (Cuno, Meriden, Conn.). RNA blots were hybridized at 42° C. for 16–18 hours with 10$^6$ cpm/ml of $^{32}$P-labeled cDNA probes, washed at 42° C. to a final stringency of 0.2× SSC, then exposed to Kodak XAR-5 films at −80° C.

cDNA Library Screening

The 60-4 probe isolated from the differential display studies (see Results) was radiolabeled and used as a probe to screen a BMCMC cDNA library, which had been constructed in our laboratory using the Uni-ZAP XR Vector (Stratagene, La Jolla, Calif.). One positive clone, SY-6, with 1.1 kb insert was isolated. To further isolate the full-length cDNA, the SY-6 clone was used as a probe to screen a mouse brain cDNA library in Uni-ZAP XR Vector purchased from Stratagene. Both libraries were screened by filter replica hybridization, and plaque-purified phages were isolated with three rounds of screening. In vivo excision of plasmids from the lamda vector was performed using ExAssist helper phage and SOLR recipient cells (Strategene).

In Vitro Transcription/Translation

Approximately 1 $\mu$g of the pBluescript SK (−) containing the full-length SY-A cDNA clone was transcribed and translated in vitro using the TNT $T_3$ Coupled Reticulocyte Lysate System (Promega). Proteins were labeled in the translation step with 40 $\mu$Ci of [$^{35}$S] methionine (1,000 Ci/mmol) (Amersham, Arlington, Ill.), run on an 8% SDS/PAGE, and visualized by autoradiography.

Generation of Stable Transfectants

The SY-A cDNA clone was digested with XbaI and XhoI restriction enzymes, and the entire full-length cDNA insert released was ligated to the pBK-CMV expression vector (Stratagene) to generate the rin2 antisense expression plasmid, pBK-CMV-SYAS. Plasmid pBK-CMV-SYAS and the vector control plasmid pBK-CMV were transfected into Cl.MC/C57.1 mast cells or PC12 cells using LIPO-FECTAMINE Reagent (Life Technologies, Gaithersburg, Md.) according to the manufacturer's instructions. For Cl.MC/C57.1 cells, transfected cells were selected in Geneticin (G418) (Life Technologies) at 2 mg/ml for 10 days and then at 0.8 mg/ml thereafter. G418-resistant mast cell colonies were observed approximately two weeks after transfection. For PC12 cells, transfected cells were selected in 0.6 mg/ml G418 and G418-resistant colonies were observed six weeks after transfection.

Measurement of Mediator Release

The release of 5-HT from mast cells was measured as previously described (Coleman et al., *J. Immunol.* 150:556–562 (1993)). Specifically, $^3$H-hydroxytryptamine creatinine sulfate (25.2 Ci/mmol) (NEN) was added to mast cells 2 hours before stimulation. The cells were washed to remove unincorporated $^3$H-5-HT and stimulated with IgE and specific antigen as described above. Release of radioactivity in supernatant fractions (150 $\mu$l) was determined after stimulation, and net percentage release was calculated as [(a−b)÷c]×100, where "a" is radioactivity released by stimulated cells, "b" is radioactivity released by unstimulated cells, and "c" is total incorporated cellular radioactivity that was measured after cells were lysed in 0.05% Triton X-100 (Sigma). IL-6 release was assayed using enzyme-linked immunosorbent assay ELISA kits (ENDOGEN, Boston, Mass.) according to the manufacturer's instructions.

MAP Kinase Assay

The p44/p42 Erk-MAP kinase activity was assayed using the MAP Kinase Assay Kit (New England Biolabs, Beverly, Mass.). Specifically, cells were lysed by sonication in 0.5 ml of cell lysis buffer (20 mM Tris 7.5, 150 mM NaCl, 1 mM EDTA, 1 mM EGTA, 1% Triton X-100, 2.5 mM sodium pyrophosphate, 1 mM β-glycerolphosphate, 1 mM $Na_3VO_4$ 1 μg/ml leupeptin, 1 mM PMSF). 0.2 ml of cell lysate was then incubated with the phospho-specific p44/p42MAP kinase antibody (1:100 dilution) overnight at 4° C. and subsequently with Protein A/G PLUS-Agarose (Santa Cruz Biotechnology, Sant Cruz, Calif.) for 3 hours at 4° C. Immunoprecipitates were incubated in 50 μl 1× kinase buffer (25 mM Tris 7.5, 5 mM β-glycerolphosphate, 2 mM DTT, 0.1 mM $Na_3VO_4$, 10 mM $MgCl_2$) supplemented with 100 mM ATP and 1 μg of Elk1 fusion protein substrate for 30 minutes at 30° C. The reaction mixture was subjected to 12% SDS-PAGE gel electrophoresis, and then electroblotted onto Immobilon-P transfer membrane (Millipore, Bedford, Mass.). Membranes were incubated with the phospho-specific Elk1 (Ser383) antibody (1:1000 dilution), and the antibody was visualized with horseradish peroxidase-conjugated anti-rabbit IgG secondary antibody using the Phototope-HRP Western Detection Kit (New England Biolabs, Beverly, Mass.). The films were subsequently scanned using a densitometer (Molecular Dynamics, Sunnyvale, Calif.) and specific signals for phospho-Elk1 were quantitated by ImageQuant software (Molecular Dynamics).

Statistical Analysis

The results for differences in mediator release were analyzed for statistical significance by the unpaired Student's t test (two-tailed). All results are expressed as the arithmetic mean±SEM.

Results

Identification of a Differentially-Expressed mRNA in Mouse Mast Cells Stimulated with IgE and Antigen To isolate genes involved in FcεRI-mediated signaling, the Cl.MC/C57.1 cell line, a cloned growth factor-independent mouse mast cell line of BALB/c origin (Young et al., *Proc. Natl. Acad. Sci. USA* 84:9175–9179 (1987); Tsai et al., *FASEB J.* 10, Abstract A1268 (1996)), was used. It has been reported that Cl.MC/C57.1 cells can exhibit many functional cellular responses characteristic of activated mast cells, including the release of pre-formed mediators and cytokines upon FcεRI receptor crosslinking (Gordon and Galli, *J. Exp. Med.* 174:103–107 (1991)). Cl.MC/C57.1 mast cells were sensitized with anti-DNP IgE mAb and challenged with $DNP_{30-40}HSA$ or vehicle alone for 30 minutes, 1 hour, or 2 hours. Total RNAs were extracted from the stimulated or unstimulated mast cells, and subjected to mRNA differential display analysis as described (Liang and Pardee, *Science* 257:967–971 (1992); Liang et al., *Nucl. Acids Res.* 21:3269–3275 (1993)).

Twenty-six differential display experiments were performed using different combinations of 3' anchored primers and 5' arbitrary primers and different RNA isolates from various time intervals of stimulation. Total RNA was extracted from Cl.MC/C57 mast cells that had been activated by IgE and specific antigen for 1 hour, and then amplified using $T_{12}MT$ anchored primers and the AP-5 arbitrary primer (5'-GTTGCGATCC) (SEQ ID NO: 7). Several differentially expressed bands were consistently detected, including band 60-4.

Band 60-4 was excised from the gel, reamplified, and used as probe for subsequent Northern blot analysis. The 60-4 cDNA probe hybridized to a 2.8 kb mRNA whose expression was rapidly increased in Cl.MC/C57.1 mouse mast cells that had been activated through the FcεRI for 30 minutes or 1 hour, but returned to baseline levels after 2 hours. The 60-4 probe was subsequently subcloned, and sequence analysis revealed a 328 base pair cDNA with no significant homology to any other entry in the Genbank database.

Cloning and Structure of Murine Rin2

The 60-4 probe was used to screen a BALB/c mouse bone marrow-derived cultured mast cell (BMCMC) cDNA library constructed in the Uni-ZAP XR vector (Stratagene). One positive clone (SY-6) with a 1.1 kb insert was isolated. Sequencing of the entire SY-6 partial cDNA clone revealed no significant homology with any known genes. To facilitate the cloning of the full-length cDNA, the SY-6 clone was used as a probe to assess the expression pattern of the identified novel gene transcript by Northern blot analysis. The expression of this novel mRNA appeared widespread, as it was detected in many tissues, including the brain. Because the identified gene transcript was expressed fairly abundantly in the brain, the SY-6 partial cDNA clone was used to screen a mouse brain cDNA library (Stratagene) in an attempt to obtain the full-length cDNA clone. Three positive clones (SY-A, SY-B, SY-C) were identified after the tertiary screening, and clone SY-A appeared to contain an insert (2.6 kb) of the appropriate predicted size (2.8 kb).

Sequencing of the entire SY-A clone (2664 base pairs) revealed a potential translational initiation codon (ATG) at base 60 and a stop codon (TGA) at base 1534. The predicted open reading frame (ORF) of 1476 base pairs encodes a predicted protein of 492 amino acids with a molecular mass of 56.9 kDa (FIG. 3). To determine whether the SY-A cDNA could indeed express a protein of the predicted size, the SY-A clone was subcloned into a pGEM expression vector and subjected to coupled in vitro transcription/translation in a wheat germ lysate system. A specific product of an apparent molecular mass of 60 kDa was detected. These results are thus consistent with the size of the predicted protein deduced from the predicted ORF. Moreover, hydrophilicity plot (Kyte-Doolittle) analysis of the predicted ORF revealed a highly hydrophilic protein with a few short hydrophobic regions. Thus, the protein product of the predicted ORF is likely to be a soluble cytosolic protein.

The predicted amino acid sequence of SY-A cDNA was used to search available protein databases using the BLAST program network server. Over a particular stretch of amino acid sequence, the SY-A gene product was found to share significant sequence homology with members of a putative GTPase-binding protein family such as Vps9p (BLAST P=2.2e−19), JC265 (P=5.2e−05), and Rin1 (P=4.1e−05) (FIG. 4). Vps9p is a recently characterized yeast protein required for vacuolar protein sorting (Burd et al., *Mol. Cell. Biol.* 16:2369–2377 (1996)). The two mammalian proteins encoded by two closely related human cDNAs, JC265 and Rin1, have been identified as inhibitors of an activated Ras2 allele in *S. cerevisiae* (Colicelli et al., *Proc. Natl. Acad. Sci. USA* 88:2913–2917 (1991); Han and Colicelli, *Mol. Cell. Biol.* 15:1318–1323 (1995)). Alignment of the amino acid sequences of these proteins with that of SY-A showed that the highest homology was found in the GTPase binding homology (GBH) domain regions in which three GBH motifs have been described (Burd et al., *Mol. Cell. Biol.* 16:2369–2377 (1996)). Specifically, the SY-A protein contains a 148-amino acid sequence which is 34% identical (51/148) and 22% similar (33/148) to the respective GBH domains of Vps9p containing the three GBH motifs (FIG. 4). Moreover, the SY-A gene product contains an amino acid sequence (SADDFLPTL; SEQ ID NO: 8) that matches well with the proposed GBH motif II (GADXFLPVL; SEQ ID NO: 9), and another downstream sequence (GEDGYYFTN; SEQ ID NO: 10) that also aligns well with the proposed GBH motif III (GEXXYYLTS; SEQ ID NO: 11) (Burd et al., *Mol. Cell. Biol.* 16:2369–2377 (1996)) (FIG. 4). Interestingly, the GBH motif II is situated in a region of JC265 and Rin1 that has been previously suggested to be distantly related to several Ras-interacting proteins such as the human GAP, the yeast IRA1 and IRA2 proteins, NF1, and sar1 (Colicelli et al., *Proc. Natl. Acad. Sci. USA* 88:2913–2917 (1991)). Because of its significant homology to the mammalian protein Rin1, the protein encoded by the SY-A cDNA is herein called Rin2, and the gene encoding the protein is herein called rin2.

Decreased Expression of Rin2 Enhances Signaling Responses Induced by FcϵRI Aggregation in Mast Cells The FcϵRI-induced activation of Ras in mast cells results in an increase in transcriptional activity of the transcription factor Elk-1 (Turner and Cantrell, *J. Exp. Med.* 185:43–53 (1997)), which is a regulator of the serum response element in the promoter region of immediate early response genes such as c-fos (Treisman, *Curr. Opin. Genet. Dev.* 4:96–101 (1994)). The transcription activation of Elk-1 is mediated by the Ras/Raf-1/MEK/Erk-MAP kinases pathway (Treisman, *Curr. Opin. Cell Biol.* 8:205–215 (1996)). As described herein, rin2 mRNA was identified by virtue of its enhanced expression in mast cells that are activated by FcϵRI aggregation. Because Rin1 has been indicated as a negative effector of Ras, the ability of Rin2 to suppress the signaling responses initiated by Ras in mouse mast cells activated by FcϵRI ligation was assessed.

The SY-A cDNA was inserted into a CMV expression vector (pBK-CMV) in the antisense orientation, and the resulting plasmid (pBK-CMV-SYA-AS) was stably transfected into mouse Cl.MC/C57.1 mast cells. The G418-resistant colonies obtained were stimulated with IgE and antigen, and the pattern of expression of early response genes such as c-fos was assessed using Northern blot analysis. Transfection of antisense rin2 significantly enhanced the expression of mRNA of c-fos in mouse mast cells activated by FcϵRI crosslinking. In mouse mast cells transfected with the control CMV plasmid, c-fos mRNA expression was rapidly induced by 15 or 30 minutes after IgE and antigen-dependent stimulation, but returned to undetectable or basal levels by 1 hour after stimulation. In contrast, in mouse mast cells transfected with the rin2 antisense construct, not only was a significantly higher level of c-fos expression observed at 15 or 30 minutes after IgE and antigen-dependent stimulation, but a significant and sustained induction of c-fos message was still detectable in these activated mast cells at 1 hour after stimulation.

Figure 5:
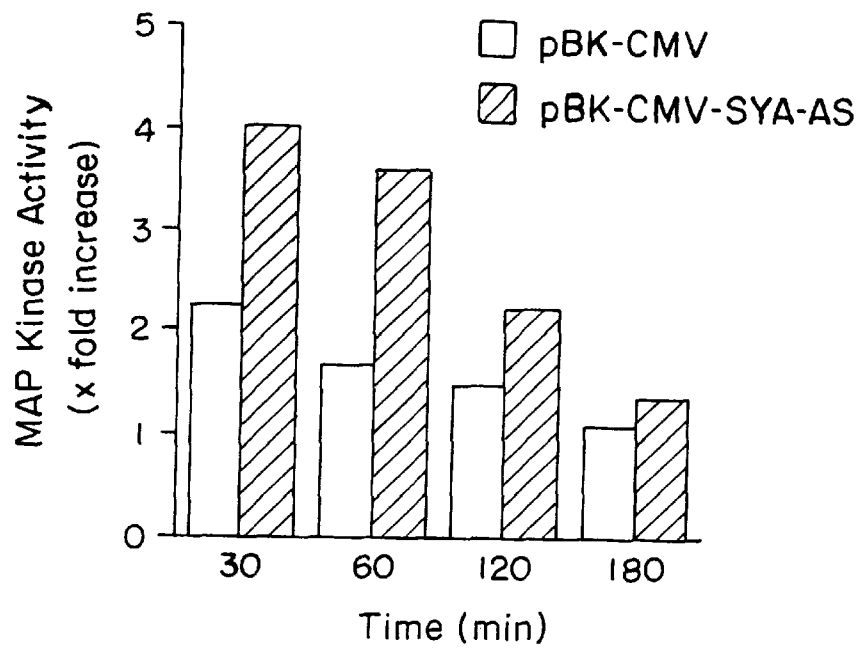
FIG. 5 is a graph of the kinetics of Erk-MAP kinase activation induced by FcεRI aggregation in Cl.MC/C57.1 mast cells transfected with the control vector (pBK-CMV) or in Cl.MC/C57.1 cells transfected with the antisense expression vector (pBK-CMV-SYA-AS).

Similarly, the activation of Erk-MAP kinase activity induced by FcϵRI activation was also greatly potentiated in Cl.MC/C57.1 mast cells that had been stably transfected with the antisense rin2 construct (FIG. 5). Consistent with results reported previously (Tsai et al., *Eur. J. Immunol.* 23:3286–3291 (1993), FcϵRI crosslinking caused a rapid activation of Erk-MAP kinase activity in mouse mast cells which had been transfected with the control plasmid 30 minutes after stimulation (2.2 fold increase). The activation persisted for 2 hours (approximately 1.5 fold increase) and then declined to basal levels by 3 hours after stimulation (1.0 fold). In contrast, in mouse mast cells transfected with the rin2 antisense plasmid, a significantly higher level of Erk-MAP kinase activation was induced by FcϵRI-dependent stimulation for 30 minutes (4.0 fold), 1 hour (3.6 fold), or 2 hours (2.2 fold) after the addition of antigen, and such Erk-MAP kinase activation was still sustained at 3 hours (1.3 fold). Taken together, the results of these studies indicate that reduced expression of Rin2 can result in marked potentiation of the Ras-mediated signaling responses in mast cells, and suggest that Rin2 functions as a Ras inhibitor/effector.

Figure 6:
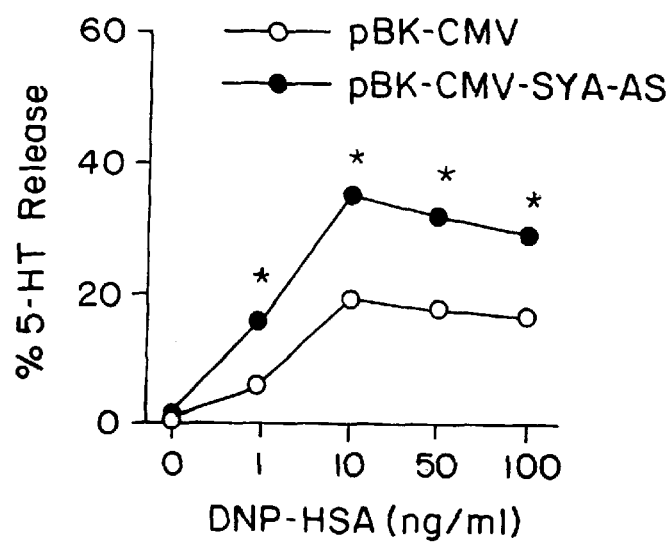
FIG. 6 is a graph of the release of $^3$H-serotonin induced by FcεRI aggregation in Cl.MC/C57.1 mast cells transfected with the control vector (pBK-CMV) or in Cl.MC/C57.1 cells transfected with the antisense expression vector (pBK-CMV-SYA-AS). Release of serotonin, assessed as percentage of specific release of [$^3$H]-5HT, was measured 10 minutes after challenge. An asterisk indicates $P<0.05$ versus corresponding values for cells transfected with the control pBK-CMV vector (n=4 to 5 per point).

Decreased Expression of Rin2 Potentiates Release of Preformed Mediator from Mast Cells Activated by FcϵRI Aggregation Since reduced expression of Rin2 can potentiate some of the intracellular signaling responses initiated by FcϵRI-dependent mast cell activation, the effect of decreased Rin2 expression on the cells' secretory responses to FcϵRI-dependent activation was also assessed. Cl.MC/C57.1 mast cells which had been transfected with the rin2 antisense expression or control vectors were stimulated with IgE and $DNP_{30-40}HSA$. As shown in FIG. 6, mouse mast cells stably transfected with the rin2 antisense construct released significantly higher levels of the preformed mediator, 5-HT, than did mast cells transfected with the pBK-CMV vector only. This effect was observed at all concentrations of DNP antigen tested (1, 10, 50, or 100 ng/ml $DNP_{30-40}HSA$), indicating that the potentiating effect of rin2 antisense expression was not antigen dose-dependent.

Figure 7A:
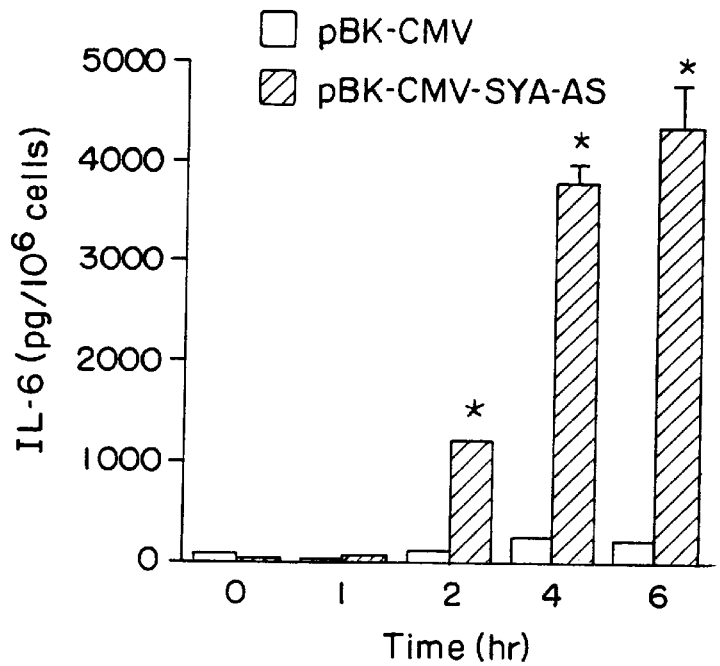
FIGS. 7A and 7B are graphs of the kinetics of IL-6 release by mast cells.
Figure 7B:
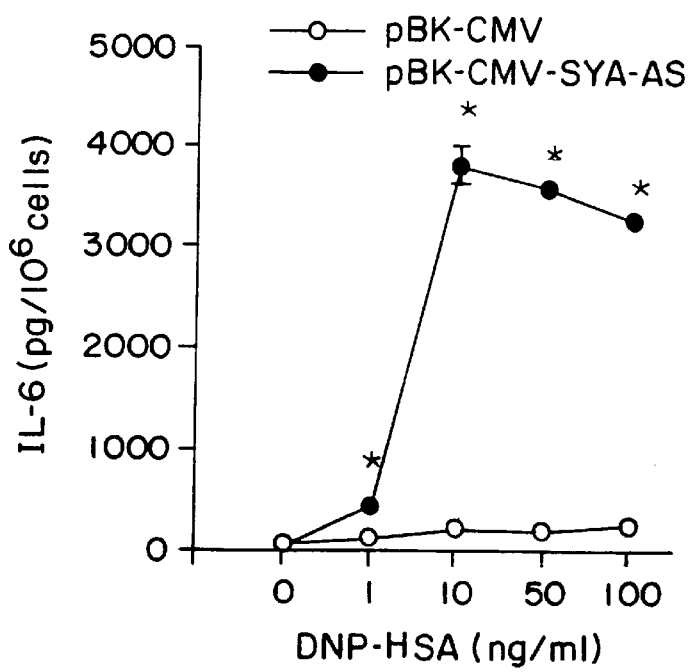

Decreased Expression of Rin2 Potentiates Cytokine Release from Mast Cells Activated by FcϵRI Aggregation Crosslinking of FcϵRI receptors not only induces mast cells to release preformed mediators such as 5-HT, but also induces these cells to secrete cytokines (Gordon et al., *Immunol. Today* 11:458–464 (1990); Paul et al., *Adv. Immunol.* 53:1–29 (1993)). Thus, the effect of changes in Rin2 expression on the FcϵRI-dependent release of IL-6 from mouse mast cells was also assessed. As illustrated in FIG. 7A, the release of IL-6 from mast cells 2, 4, or 6 hours after FcϵRI aggregation (50 ng/ml) was enhanced dramatically by the transfection of the cells with the rin2 antisense expression vector, as compared with responses elicited in mast cells transfected with the control CMV vector. This potentiating effect was more pronounced (greater than 20-fold increase) in cells which had been stimulated for longer time intervals (4–6 hours). Furthermore, when the transfected cells were stimulated by different concentrations of $DNP_{30-40}HSA$ for 6 hours, mouse mast cells which had been transfected with the rin2 antisense construct released significantly higher levels of IL-6 than did mast cells which had been transfected with the control vector at each concentration of antigen tested (FIG. 7B).

Rin2 mRNA Expression is Up-regulated in Mouse Mast Cells Stimulated with Stem Cell Factor and in PC12 Cells Stimulated with Nerve Growth Factor To assess whether the enhanced expression of the rin2 transcript was specific for the FcϵRI-dependent signaling pathway in mast cells, Northern analysis was performed to examine the expression of rin2 mRNA in mouse bone marrow derived cultured mast cells (BMCMC) which had been stimulated with the growth factor, stem cell factor (SCF), the ligand for the c-kit receptor tyrosine kinase (Galli et al., *Adv. Immunol.* 55:1–96 (1994)). The widespread tissue distribution of rin2 mRNA suggests that Rin2 may function as a signaling element in the functional responses of many cell types besides mast cells. Therefore, rin2 expression was also analyzed in PC12 cells, an adrenal pheochromocytoma cell line, which had been stimulated with nerve growth factor (NGF) (Greene and Tischler, *Proc. Natl. Acad. Sci. USA* 73:2424–2428 (1976)).

rin2 mRNA expression was rapidly increased by 30 minutes to 1 hour after stimulation of BMCMCs with SCF (50 ng/ml), but returned nearly to baseline levels after 2 hours. Expression of the rin2 transcript was also significantly induced 30 minutes after NGF stimulation (50 ng/ml) in PC12 cells, and the enhanced expression of the transcript was still detectable 2 hours after stimulation. Thus, SCF induced a transient enhancement of rin2 mRNA expression in mast cells, but NGF elicited a much more sustained activation of rin2 expression in PC12 adrenal pheochromocytoma cells.

Decreased Expression of Rin2 Enhances Cell Proliferation in PC12 Cells

Figure 8A:
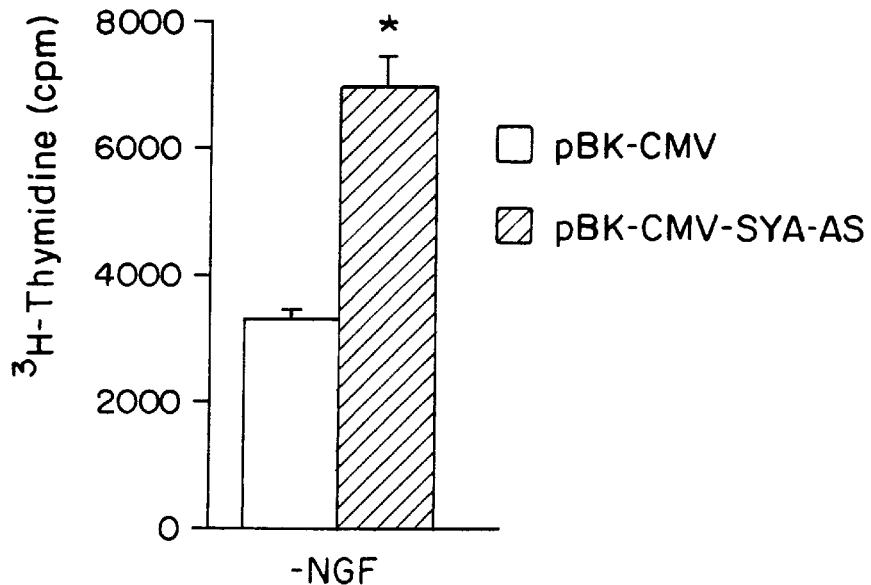
FIGS. 8A and 8B are graphs illustrating that expression of antisense rin2 mRNA enhances cell proliferation in PC12 cells, a rat adrenal pheochromocytoma cell line. Rate of proliferation of PC12 cells transfected with rin2 antisense expression vector (pBK-CMV-SYA-AS), or PC12 cells transfected with the control CMV vector (pBK-CMV), or untransfected PC12 cells, was measured by assessing [$^3$H] thymidine incorporation in cells which had been incubated with [$^3$H] thymidine for 3 hours after the cells had been cultured overnight in normal culture medium (FIG. 8A), or in medium containing nerve growth factor (NGF) of indicated concentrations and 0.5% FCS (+NGF.
Figure 8B:
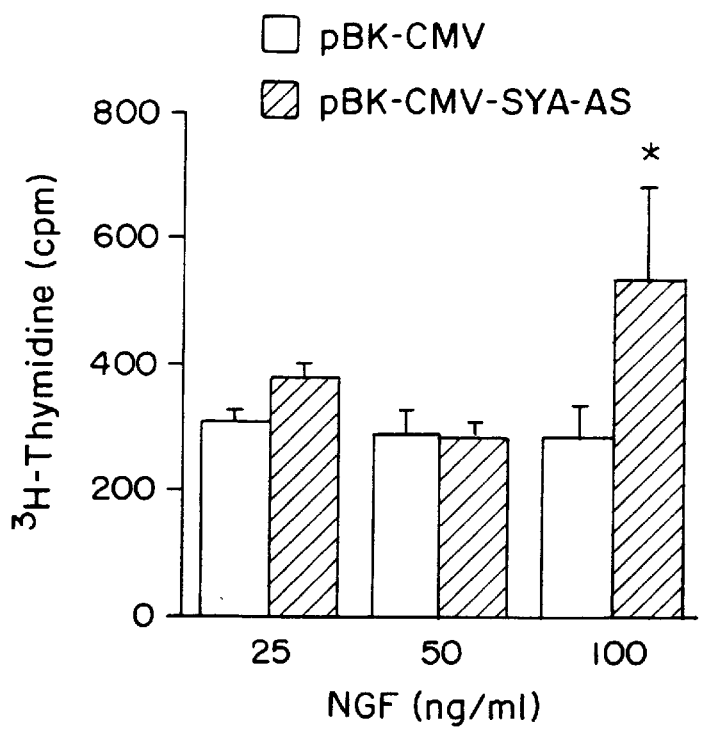

PC12 cells stimulated with NGF undergo neuronal differentiation, which is characterized by the extension of neurites and the cessation of cell proliferation (Greene and Tischler, *Proc. Natl. Acad. Sci. USA* 73:2424–2428 (1976)). Since NGF promoted a sustained induction of rin2 mRNA expression in PC12 cells, the effects of reduced rin2 expression on cell proliferation rate and NGF-induced neurite outgrowth were examined in these cells. The antisense expression vector pBK-CMV-SYA-AS was stably transfected into PC12 cells, and the transfected cells were plated onto collagen-coated plates and stimulated with NGF at 25, 50 or 100 ng/ml. After 3–5 days, neurite outgrowth was observed both in PC12 cells that had been transfected with the antisense expression vector and in those cells that had been transfected with the control CMV vector. No detectable differences in the time of onset or the number of neurite-bearing cells could be observed between these populations of transfected cells. These results thus indicate that Rin2 may not be directly involved with NGF-induced neuronal differentiation in PC12 cells. On the other hand, PC12 cells which had been transfected with the antisense expression vector and then maintained in their normal culture medium exhibited a significantly higher rate of cell proliferation, as measured by a $^3$H-thymidine assay, than did the cells which had been transfected with the control pBK-CMV vector (FIG. 8A). This effect was also observed when the transfected PC12 cells were stimulated with NGF (100 ng/ml) for 18 hours in medium containing 0.5% FCS (FIG. 8B). Since NGF is known to be anti-mitogenic to PC12 cells (Greene and Tischler, *Proc. Natl. Acad. Sci. USA* 73:2424–2428 (1976)), these results are consistent with the hypothesis that Rin2 expression results in the inhibition of cell proliferation in PC12 cells and perhaps other neuronal cells.

Rin2 mRNA Expression is Up-Regulated in EL-4 T Cells Stimulated via the T Cell Receptor Complex The binding of peptide antigen and major histocompatibility complex molecules to the T cell receptor (TCR) induces T cell activation, which includes the secretion of effector cytokines by the T cells and the induction of mitotic activity in the T cells themselves. Extensive evidence has shown that the activation of Ras is involved in some of the intracellular signaling pathways mediating T cell activation (Lowy and Willumsen, *Ann. Rev. Biochem.* 62:851–891 (1993)). To assess whether T cell activation could result in enhanced expression of the rin2 transcript, Northern analysis was performed to examine the expression of rin2 mRNA in EL-4 mouse T cells that had been stimulated via the TCR by incubating the cells with both anti-CD3 antibody (1 μg/ml) and anti-CD28 antibody (2 μg/ml). rin2 mRNA expression was rapidly increased by 30 minutes to 1 hour after TCR stimulation, but declined nearly to baseline levels after 2 hours. The time course of this effect on rin2 mRNA expression in T cells is thus similar to that observed in mouse mast cells stimulated with SCF or IgE and antigen.

Equivalents

Those skilled in the art will recognize, or be able to ascertain, using no more than routine experimentation, many equivalents to the specific embodiments of the invention described herein. Such equivalents are intended to be encompassed by the following claims:

We claim:

1. An isolated Rin2 polypeptide which down-regulates functional responses elicited by ligand-dependent activation, or auto activation, of Ras-mediated signaling pathways, wherein said polypeptide comprises at least one sequence selected from the group consisting of: SEQ ID NO: 8, SEQ ID NO; 10, SEQ ID NO: 12 and combinations thereof.

2. An isolated Rin2 polypeptide comprising the amino acid sequence of SEQ ID NO: 2, which polypeptide down-regulates functional responses elicited by ligand-dependent activation, or auto activation, of Ras-mediated signaling pathways.

3. An isolated Rin2 polypeptide according to claim 2, wherein the down-regulated functional response is selected from the group consisting of: proliferation, differentiation, release of mediators, release of cytokines, and T cell functional responses.

4. An isolated Rin2 polypeptide according to claim 3, wherein the down-regulated functional response results from ligand-dependent activation, or auto-activation, of a cell surface receptor selected from the group consisting of: a FcεRI receptor, a T cell receptor, a TrkA receptor and a c-kit receptor.

5. An isolated Rin2 polypeptide according to claim 4, wherein the cell surface receptor is FcεRI and the down-regulated functional response is release of mediators and cytokines in response to ligand-dependent receptor aggregation.

6. An isolated Rin2 polypeptide according to claim 3, wherein the down-regulated functional response is selected from the group consisting of: proliferation, differentiation, release of mediators, release of cytokines, and T cell functional responses.

7. An isolated Rin2 polypeptide according to claim 6, wherein the down-regulated functional response results from ligand-dependent activation, or auto-activation, of a cell surface receptor selected from the group consisting of: a FcεRI receptor, a T cell receptor, a TrkA receptor and a c-kit receptor.

8. An isolated Rin2 polypeptide according to claim 7, wherein the cell surface receptor is FcεRI and the down-regulated functional response is release of mediators and cytokines in response to ligand-dependent receptor aggregation.

* * * * *